United States Patent
Campagnari et al.

(10) Patent No.: US 7,468,256 B2
(45) Date of Patent: Dec. 23, 2008

(54) **TOOLS FOR DETECTING *MORAXELLA CATARRHALIS***

(75) Inventors: Anthony Campagnari, Hamburg, NY (US); Nicole Luke, Webster, NY (US); Kristin Furano, Amherst, NY (US); Amy Howlett, Williamsville, NY (US); Katie Edwards, Malone, NY (US)

(73) Assignee: The Research Foundation of State University of New York, Amherst, NY (US)

( * ) Notice: Subject to any disclaimer, the term of this patent is extended or adjusted under 35 U.S.C. 154(b) by 223 days.

(21) Appl. No.: 10/844,776

(22) Filed: May 13, 2004

(65) Prior Publication Data

US 2005/0142607 A1 Jun. 30, 2005

Related U.S. Application Data

(60) Provisional application No. 60/470,022, filed on May 13, 2003.

(51) Int. Cl.
- *G01N 33/569* (2006.01)
- *G01N 33/53* (2006.01)
- *C07K 16/12* (2006.01)
- *C07K 16/00* (2006.01)
- *C12P 21/08* (2006.01)
- *A61K 39/02* (2006.01)

(52) U.S. Cl. .................. 435/7.32; 435/7.2; 435/7.1; 530/391.1; 530/388.4; 530/388.2; 530/388.1; 530/387.1; 424/178.1; 424/164.1; 536/23.7; 536/23.1

(58) Field of Classification Search ............. 435/7.1, 435/7.2, 69.7, 7.32; 530/388.1, 391.1, 350, 530/388, 388.4, 388.2, 387.1; 424/163.1, 424/164.1, 178.1, 164; 536/23.7
See application file for complete search history.

(56) References Cited

U.S. PATENT DOCUMENTS 6,649,171 B1 11/2003 Thonnard

OTHER PUBLICATIONS

Rahman et al 1998, Microbial pathogenesis 24; 299-308.*
Norkus et al Clin Microbiol. Dec. 28, 1990; (12): 2815-2817.*
Oishi et al Clin Diagn Lab Immunol. May 3, 1996; (3):351-4.*
Mathers .K , Pediatr Infect Dis J. Nov. 18, 1999; (11):982-8.*
Anthony Zaleski et al , Infection and Immunity, Sep. 2000, p. 5261-5268, vol. 68, No. 9.*
M Vaneechoutte et al J Clin Microbiol. Feb. 28, 1990; (2): 182-187.*
Hu et al Infect Immun. Mar. 2001; 69(3): 1358-1363.*

* cited by examiner

*Primary Examiner*—Robert B Mondesi
*Assistant Examiner*—Padma V Baskar
(74) *Attorney, Agent, or Firm*—Hodgson Russ LLP

(57) ABSTRACT

The present invention provides compositions and methods useful for detecting *Moraxella catarrhalis*. The compositions are antibodies, proteins or nucleic acid sequences specific to *Moraxella catarrhalis* (*M. catarrhalis*). The method comprises the steps of obtaining a biological sample from an individual and detecting within the biological sample the presence of proteins, nucleic acid sequences and lipooligosaccharides (LOS) specific to *Moraxella catarrhalis*. Further, compositions and methods useful for distinguishing between *M. catarrhalis* serotypes are provided.

3 Claims, 10 Drawing Sheets

Flow Chart for LOS Serotype Analysis

Sero A.

Sero B.

Sero C.

SEQUENCE LISTING

<160> NUMBER OF SEQ ID NOS: 17

<210> SEQ ID NO 1
<211> LENGTH: 2886
<212> TYPE: DNA
<213> ORGANISM: Moraxella catarrhalis
<220> FEATURE:
<222> LOCATION:
<223> OTHER INFORMATION: MhuA gene sequence

<400> SEQUENCE: 1

```
atgatgataa caggtaatac catgaaccaa atttttcatt tgatgacaca aaccaagcat      60
acaaatcaca ccaaaaaggt gctaaaactg agcatgctgt ccttgtgttt gctacacatc     120
acccaaactg ccatggcaga ggatacccct aaggatgtgc caaaagcaac ggattttcct     180
gtcatcttag atgaggttgt tgtaacggcg accaacggca ccaaaaaatc ccaaaaaccc     240
tttaccaaag catcggccac cagcgtgcga gaaaatgtat ttaatgccag tgagaatatt     300
gatgccattg tgcgcagtgt gccaggggcg tttactcagc aggataaatc ctctgggctg     360
gtatcattaa atgtacgagg cgatagtgga tttggcgtg ccaatagcat ggttgatggt      420
gtaacccaaa ccttttacag cacctcaacc gatgctgggc gtggggggtgg cacctcacag    480 tttggtgcgg tgattgacca aaatttcatt gcaggcgttg aattaaacaa aggcagtttt     540
aatggcaaag gtggtctaaa taccttaaca ggttcggcca attttcgtac gctaaatgct     600
gatgatgtga ttaaagatga caaaaatttt ggcttcattg ccaagggttt gaccggtaaa     660
aatgcgacgg ataaaaattt tatgctggca gctggcggac gtggatggct tgataatggc     720
agtatcagtg ctttatatgc ttatagccac aaagacatta gccaaaatta taagttggc      780 ggtggcggga cgcacattgg caatgttggt gatgatttgc tacttagtaa acaaaaacaa     840
gtttttgcca agagcatgc actcacttac aatgaagcca gccgttcctg caaaaagat      900 ttgaccaaat tagataaaga acaggcaag cctttatggg acagaaaata tcaatttggc      960
ggtaagtgct atgggctggg ctgtattgat acaaagagaa gtttgatga atatgttgct     1020 gacaaacagc agcagtggca aaagcatggt gcaaagagt acagcatcac ccccattgat     1080
atcaccgccc taaccaaac ctcaaaaagc catttggcaa aaattcgtta caacaatgac     1140
accagcgatg ttggtctaca actgcgtaaa atggacacca cgataggcag tcgccgtatc     1200
agcaatgata ttatcaact tgatgctgct tacaacccaa atgagatcat tgatttaaaa     1260
gtgttggcag cccataatgt gggcgtacaa aaataccca aaggttcaac ttttacaggc     1320
tggaaattgg ataaagactt tgaaaccaaa aacactgcca atcttttttga cctgaacaac     1380 actcacacct ttaatctgcc aaagcaaatg gatttgacca caaccgttgg gctgaacata     1440
ttgcataatg aatattcaaa aaatcgcttc ccagatgagc ttgggctatt ttataccaat     1500
gatttattat gtggcggcgg ttatgatgcc tgtggtggtc gttttcaggg gacaagcagc     1560
acactgccaa aaaatcggt gattgtacag ccctcaggca acagcgtttt cattctatt     1620 tatttggaca tcattacaa aaagacaaaa tatcagttag attatagcgt taatgccagt     1680
cagtaccgtt ttagtggtga gcatgccagt tattatagca gccaaaaga gtttcaagat     1740 aagtttggtg aagattcgca aatttataaa cagcactgct cgccaagttg tgatgtgtat    1800
gagcctttgg taaccactc tggtaaaaaa cacgccatca accattctgt tactttaagt     1860
gccaaatatg acacaggttt tatgcctttt gtcagctttg cacgcacgca cagaatgccc    1920
```

-continued

```
aacattcaag aaatgttctt ttctcaaatt ggtgatgttg gcgtcaatac tgcattaaaa    1980
ccagagcaag ccaatacata tcagttgggt tttaatgttt ttaaacgcaa tctattgaca    2040
gacaacgata ctttggggct aaaagtagtg ggttatcaaa gccgtattaa caattacatt    2100
cataatgttt atggtaaatg gtatgacaca aaaaatccac ccagttgggt gaccagtggt    2160
gcattaaaag gcgataccat acagcatcgc aattggcaaa tgcctgtgca taaacagggc    2220
ttagagcttg aaatcaacta tgatgctggg cggtatttta ccaatttgtc ttatgccaga    2280
caaaagaccg accagccaac caattatagc gatgccagcg agtccccacg aaatagctca    2340
aaagaagacc aattaaccca aggctatggg ctaagcaaag tgtcaatgtt gcccaaagat    2400
tatggtcgtt ttgaacttgg tgtgcgtggc tttgatgaca aactcaccat aggcagtgcg    2460
gtgcgttatt atggacaaag cccacgagcg accattgaac ccagatacat tgatggcacg    2520
catggtggca atacatcgca ttcagatgat aaaggtgctc atgtcatcaa gcaaattgag    2580
atgctaaaaa gacagccttt ggtgcatgat ttttatgttg cttatgagcc aataaaagat    2640
ttggtgatgc gtcttgatgt gcaaaatgcg tttgataaac tgtatattga ccccttagat    2700
gccaacaatg atgccgccac tcagcgttat tatcattcat attataatga tgcagacgaa    2760
ggcgcacctt gtgcagcggg gcagttgtgt aagcctgatg caaaatacgg cggtactact    2820
cgctcggtat tgaccaattt tgccaaaggg cgttctttat tatcttcaat gacttataag    2880
tggtag                                                                2886
```

<210> SEQ ID NO 2
<211> LENGTH: 961
<212> TYPE: PRT
<213> ORGANISM: Moraxella catarrhalis
<220> FEATURE:
<223> OTHER INFORMATION: MhuA protein

<400> SEQUENCE: 2

```
Met Met Ile Thr Gly Asn Thr Met Asn Gln Ile Phe His Leu Met
                5                  10                  15

Thr Gln Thr Lys His Thr Asn His Thr Lys Lys Val Leu Lys Leu
                20                  25                  30

Ser Met Leu Ser Leu Cys Leu Leu His Ile Thr Gln Thr Ala Met
                35                  40                  45

Ala Glu Asp Thr Leu Lys Asp Val Pro Lys Ala Thr Asp Phe Ser
                50                  55                  60

Val Ile Leu Asp Glu Val Val Thr Ala Thr Asn Gly Thr Lys
                65                  70                  75

Lys Ser Gln Lys Pro Phe Thr Lys Ala Ser Ala Thr Ser Val Arg
                80                  85                  90

Glu Asn Val Phe Asn Ala Ser Glu Asn Ile Asp Ala Ile Val Arg
                95                  100                 105

Ser Val Pro Gly Ala Phe Thr Gln Gln Asp Lys Ser Ser Gly Leu
                110                 115                 120

Val Ser Leu Asn Val Arg Gly Asp Ser Gly Phe Gly Arg Ala Asn
                125                 130                 135

Ser Met Val Asp Gly Val Thr Gln Thr Phe Tyr Ser Thr Ser Thr
                140                 145                 150

Asp Ala Gly Arg Gly Gly Gly Thr Ser Gln Phe Gly Ala Val Ile
                155                 160                 165

Asp Gln Asn Phe Ile Ala Gly Val Glu Leu Asn Lys Gly Ser Phe
                170                 175                 180
```

-continued

```
Asn Gly Lys Gly Gly Leu Asn Thr Leu Thr Gly Ser Ala Asn Phe
            185                 190                 195
Arg Thr Leu Asn Ala Asp Asp Val Ile Lys Asp Asp Lys Asn Phe
            200                 205                 210
Gly Phe Ile Ala Lys Gly Leu Thr Gly Lys Asn Ala Thr Asp Lys
            215                 220                 225
Asn Phe Met Leu Ala Ala Gly Gly Arg Gly Trp Leu Asp Asn Gly
            230                 235                 240
Ser Ile Ser Ala Leu Tyr Ala Tyr Ser His Lys Asp Ile Ser Gln
            245                 250                 255
Asn Tyr Lys Val Gly Gly Gly Thr His Ile Gly Asn Val Gly
            260                 265                 270
Asp Asp Leu Leu Leu Ser Lys Gln Lys Gln Val Phe Ala Lys Glu
            275                 280                 285
His Ala Leu Thr Tyr Asn Glu Ala Ser Arg Ser Trp Gln Lys Asp
            290                 295                 300
Leu Thr Lys Leu Asp Lys Glu Thr Gly Lys Pro Leu Trp Asp Arg
            305                 310                 315
Lys Tyr Gln Phe Gly Gly Lys Cys Tyr Gly Leu Gly Cys Ile Asp
            320                 325                 330
Thr Lys Glu Lys Phe Asp Glu Tyr Val Ala Asp Lys Gln Gln
            335                 340                 345
Trp Gln Lys His Gly Ala Lys Glu Tyr Ser Ile Thr Pro Ile Asp
            350                 355                 360
Ile Thr Ala Leu Asn Gln Thr Ser Lys Ser His Leu Ala Lys Ile
            365                 370                 375
Arg Tyr Asn Asn Asp Thr Ser Asp Val Gly Leu Gln Leu Arg Lys
            380                 385                 390
Met Asp Thr Thr Ile Gly Ser Arg Arg Ile Ser Asn Asp Asn Tyr
            395                 400                 405
Gln Leu Asp Ala Ala Tyr Asn Pro Asn Glu Ile Ile Asp Leu Lys
            410                 415                 420
Val Leu Ala Ala His Asn Val Gly Val Gln Lys Tyr Pro Lys Gly
            425                 430                 435
Ser Thr Phe Thr Gly Trp Lys Leu Asp Lys Asp Phe Glu Thr Lys
            440                 445                 450
Asn Thr Ala Asn Leu Phe Asp Leu Asn Asn Thr His Thr Phe Asn
            455                 460                 465
Leu Pro Lys Gln Met Asp Leu Thr Thr Thr Val Gly Leu Asn Ile
            470                 475                 480
Leu His Asn Glu Tyr Ser Lys Asn Arg Phe Pro Asp Glu Leu Gly
            485                 490                 495
Leu Phe Tyr Thr Asn Asp Leu Leu Cys Gly Gly Gly Tyr Asp Ala
            500                 505                 510
Cys Gly Gly Arg Phe Gln Gly Thr Ser Ser Thr Leu Pro Lys Lys
            515                 520                 525
Ser Val Ile Val Gln Pro Ser Gly Lys Gln Arg Phe His Ser Ile
            530                 535                 540
Tyr Leu Asp Thr Ser Leu Gln Lys Asp Lys Tyr Gln Leu Asp Tyr
            545                 550                 555
Ser Val Asn Ala Ser Gln Tyr Arg Phe Ser Gly Glu His Ala Ser
            560                 565                 570
```

```
Tyr Tyr Ser Ser Gln Lys Glu Phe Gln Asp Lys Phe Gly Glu Asp
            575                 580                 585

Ser Gln Ile Tyr Lys Gln His Cys Ser Pro Ser Cys Asp Val Tyr
            590                 595                 600

Glu Pro Leu Val Thr Thr Ser Gly Lys Lys His Ala Ile Asn His
            605                 610                 615

Ser Val Thr Leu Ser Ala Lys Tyr Asp Thr Gly Phe Met Pro Phe
            620                 625                 630

Val Ser Phe Ala Arg Thr His Arg Met Pro Asn Ile Gln Glu Met
            635                 640                 645

Phe Phe Ser Gln Ile Gly Asp Val Gly Val Asn Thr Ala Leu Lys
            650                 655                 660

Pro Glu Gln Ala Asn Thr Tyr Gln Leu Gly Phe Asn Val Phe Lys
            665                 670                 675

Arg Asn Leu Leu Thr Asp Asn Asp Thr Leu Gly Leu Lys Val Val
            680                 685                 690

Gly Tyr Gln Ser Arg Ile Asn Asn Tyr Ile His Asn Val Tyr Gly
            695                 700                 705

Lys Trp Tyr Asp Thr Lys Asn Pro Pro Ser Trp Val Thr Ser Gly
            710                 715                 720

Ala Leu Lys Gly Asp Thr Ile Gln His Arg Asn Trp Gln Met Pro
            725                 730                 735

Val His Lys Gln Gly Leu Glu Leu Glu Ile Asn Tyr Asp Ala Gly
            740                 745                 750

Arg Tyr Phe Thr Asn Leu Ser Tyr Ala Arg Gln Lys Thr Asp Gln
            755                 760                 765

Pro Thr Asn Tyr Ser Asp Ala Ser Glu Ser Pro Arg Asn Ser Ser
            770                 775                 780

Lys Glu Asp Gln Leu Thr Gln Gly Tyr Gly Leu Ser Lys Val Ser
            785                 790                 795

Met Leu Pro Lys Asp Tyr Gly Arg Phe Glu Leu Gly Val Arg Gly
            800                 805                 810

Phe Asp Asp Lys Leu Thr Ile Gly Ser Ala Val Arg Tyr Tyr Gly
            815                 820                 825

Gln Ser Pro Arg Ala Thr Ile Glu Pro Arg Tyr Ile Asp Gly Thr
            830                 835                 840

His Gly Gly Asn Thr Ser His Ser Asp Lys Gly Ala His Val
            845                 850                 855

Ile Lys Gln Ile Glu Met Leu Lys Arg Gln Pro Leu Val His Asp
            860                 865                 870

Phe Tyr Val Ala Tyr Glu Pro Ile Lys Asp Leu Val Met Arg Leu
            875                 880                 885

Asp Val Gln Asn Ala Phe Asp Lys Leu Tyr Ile Asp Pro Leu Asp
            890                 895                 900

Ala Asn Asn Asp Ala Ala Thr Gln Arg Tyr Tyr His Ser Tyr Tyr
            905                 910                 915

Asn Asp Ala Asp Glu Gly Ala Pro Cys Ala Ala Gly Gln Leu Cys
            920                 925                 930

Lys Pro Asp Ala Lys Tyr Gly Gly Thr Thr Arg Ser Val Leu Thr
            935                 940                 945

Asn Phe Ala Lys Gly Arg Ser Leu Leu Ser Ser Met Thr Tyr Lys
            950                 955                 960

Trp
```

```
961
```

<210> SEQ ID NO 3
<211> LENGTH: 24
<212> TYPE: DNA
<213> ORGANISM: Moraxella catarrhalis
<220> FEATURE:
<222> LOCATION:
<223> OTHER INFORMATION: primer 537

<400> SEQUENCE: 3
gccaatgctt tgcctgataa tgag                                          24

<210> SEQ ID NO 4
<211> LENGTH: 23
<212> TYPE: DNA
<213> ORGANISM: Moraxella catarrhalis
<220> FEATURE:
<222> LOCATION:
<223> OTHER INFORMATION: primer 538

<400> SEQUENCE: 4
tggtgttttg actggggtgg tag                                           23

<210> SEQ ID NO 5
<211> LENGTH: 1653
<212> TYPE: DNA
<213> ORGANISM: Moraxella catarrhalis
<220> FEATURE:
<222> LOCATION:
<223> OTHER INFORMATION: Mcp67 gene

<400> SEQUENCE: 5

| | | |
|---|---|---|
| atgagcttaa ttaataaatt aaatgaacgc attacgccgc atgtcttaac ttcgattaaa | 60 |
| aatcaagatg gcgataatgc tgataaatct aatttgttaa ccgcatttta taccattttt | 120 |
| gcaggacgct tgagtaatga agatgtgtat cagcgtgcca atgctttgcc tgataatgag | 180 |
| cttgagcatg ggcatcatct gctcaatgtt gcttttagtg atgtttcaac tggtgaagat | 240 |
| cagattgctt ctttgagtaa tcaattagcc gatgaatatc atgtttcgcc agtaacggca | 300 |
| cgcaccgcaa tcgcaacggc agcacctttg gctttggcac gcattaaaga gcaagcaggt | 360 |
| gcattatctg taccgtcttt tattcgtact caattggcta agaagaaaa ccgtttgcca | 420 |
| acttgggcgc atactttatt gccagcaggg ctatttgcaa ccgctgccac aaccaccgcc | 480 |
| gagcctgtaa cgacagcctc tgctgttgtg aaagagcctg tcaaaccaag tgttgtgaca | 540 |
| gaaccagttc atccagctgc ggctaccacc ccagtcaaaa caccaactgc ccagcattac | 600 |
| gaaaacaaag aaaaaagtcc tttttctaaaa acgattctac cgattattgg attgattatt | 660 |
| tttgcaggct tggcatggct tttgttaaga gcatgtcaag acaaaccaac acctgttgcg | 720 |
| gcacctgttg cgacagatac agcacctgtg tagcgggata tgctgtaca ggcagaccca | 780 |
| acacaaacag gtgttgccca agcacctgca acgcttagct tgtctgttga tgaaacgggt | 840 |
| caagcgttgt actcgcaccg tgctcaggtt ggtagtgaag agcttgcagg tcatatccgt | 900 |
| gcagctattg ctcaagtctt tggcgtacaa gatttaacca ttcaaaatac caatgtacat | 960 |
| accgctacga tgccagcggc agaatactta ccagcaattt tgggttttgat gaaaggtgta | 1020 |
| ccaaattcaa gcgttgtgat tcatgatcat acggtacgct ttaatgcaac cacgccagaa | 1080 |
| gatgtagcaa aactggtaga gggtgctaaa aatattctac ccgctgattt tactgtagaa | 1140 |
| gcagaacctg aacttgatat taatactgcg gttgccgata gtattgaaac agcgcgtgtt | 1200 |

```
gctattgttg ctttgggtga tacggttgaa gaaaatgaga tggatatttt aatcaatgca    1260
ttaaataccc aaatcattaa ctttgcttta gactcaaccg aaattcccca agaaaataaa    1320
gaaatcttgg atttggctgc cgaaaaatta aaggcagtgc ctgaaacaac tttgcgtatc    1380
attggtcata cagacactca aggcacacat gagtataatc aagatttatc agaatctcgt    1440
gctgctgctg ttaaagagta tttggtatca aaaggtgttg ctgctgaacg cttgaacact    1500
caaggtgcaa gttttgatta ccagttgca tcaaatgcta ccgaacaagg tcgcttccaa     1560
aaccgtcgta ttgagtttgt acttttccaa gaaggtgaag caattactca agtcggtcat    1620
gctgaagatg caccaacacc tgttgcacaa aac                                 1653
```

<210> SEQ ID NO 6
<211> LENGTH: 551
<212> TYPE: PRT
<213> ORGANISM: Moraxella catarrhalis
<220> FEATURE:
<222> LOCATION:
<223> OTHER INFORMATION: Mcp67 protein

<400> SEQUENCE: 6

```
Met Ser Leu Ile Asn Lys Leu Asn Glu Arg Ile Thr Pro His Val
              5                  10                  15

Leu Thr Ser Ile Lys Asn Gln Asp Gly Asp Asn Ala Asp Lys Ser
             20                  25                  30

Asn Leu Leu Thr Ala Phe Tyr Thr Ile Phe Ala Gly Arg Leu Ser
             35                  40                  45

Asn Glu Asp Val Tyr Gln Arg Ala Asn Ala Leu Pro Asp Asn Glu
             50                  55                  60

Leu Glu His Gly His His Leu Leu Asn Val Ala Phe Ser Asp Val
             65                  70                  75

Ser Thr Gly Glu Asp Gln Ile Ala Ser Leu Ser Asn Gln Leu Ala
             80                  85                  90

Asp Glu Tyr His Val Ser Pro Val Thr Ala Arg Thr Ala Ile Ala
             95                 100                 105

Thr Ala Ala Pro Leu Ala Leu Ala Arg Ile Lys Glu Gln Ala Gly
            110                 115                 120

Ala Leu Ser Val Pro Ser Phe Ile Arg Thr Gln Leu Ala Lys Glu
            125                 130                 135

Glu Asn Arg Leu Pro Thr Trp Ala His Thr Leu Leu Pro Ala Gly
            140                 145                 150

Leu Phe Ala Thr Ala Ala Thr Thr Thr Ala Glu Pro Val Thr Thr
            155                 160                 165

Ala Ser Ala Val Val Lys Glu Pro Val Lys Pro Ser Val Val Thr
            170                 175                 180

Glu Pro Val His Pro Ala Ala Ala Thr Thr Pro Val Lys Thr Pro
            185                 190                 195

Thr Ala Gln His Tyr Glu Asn Lys Glu Lys Ser Pro Phe Leu Lys
            200                 205                 210

Thr Ile Leu Pro Ile Ile Gly Leu Ile Ile Phe Ala Gly Leu Ala
            215                 220                 225

Trp Leu Leu Leu Arg Ala Cys Gln Asp Lys Pro Thr Pro Val Ala
            230                 235                 240

Ala Pro Val Ala Thr Asp Thr Ala Pro Val Val Ala Asp Asn Ala
            245                 250                 255

Val Gln Ala Asp Pro Thr Gln Thr Gly Val Ala Gln Ala Pro Ala
```

```
                    260                 265                 270
Thr Leu Ser Leu Ser Val Asp Glu Thr Gly Gln Ala Leu Tyr Ser
                275                 280                 285
His Arg Ala Gln Val Gly Ser Glu Glu Leu Ala Gly His Ile Arg
                290                 295                 300
Ala Ala Ile Ala Gln Val Phe Gly Val Gln Asp Leu Thr Ile Gln
                305                 310                 315
Asn Thr Asn Val His Thr Ala Thr Met Pro Ala Ala Glu Tyr Leu
                320                 325                 330
Pro Ala Ile Leu Gly Leu Met Lys Gly Val Pro Asn Ser Ser Val
                335                 340                 345
Val Ile His Asp His Thr Val Arg Phe Asn Ala Thr Thr Pro Glu
                350                 355                 360
Asp Val Ala Lys Leu Val Glu Gly Ala Lys Asn Ile Leu Pro Ala
                365                 370                 375
Asp Phe Thr Val Glu Ala Glu Pro Glu Leu Asp Ile Asn Thr Ala
                380                 385                 390
Val Ala Asp Ser Ile Glu Thr Ala Arg Val Ala Ile Val Ala Leu
                395                 400                 405
Gly Asp Thr Val Glu Glu Asn Glu Met Asp Ile Leu Ile Asn Ala
                410                 415                 420
Leu Asn Thr Gln Ile Ile Asn Phe Ala Leu Asp Ser Thr Glu Ile
                425                 430                 435
Pro Gln Glu Asn Lys Glu Ile Leu Asp Leu Ala Ala Glu Lys Leu
                440                 445                 450
Lys Ala Val Pro Glu Thr Thr Leu Arg Ile Ile Gly His Thr Asp
                455                 460                 465
Thr Gln Gly Thr His Glu Tyr Asn Gln Asp Leu Ser Glu Ser Arg
                470                 475                 480
Ala Ala Ala Val Lys Glu Tyr Leu Val Ser Lys Gly Val Ala Ala
                485                 490                 495
Glu Arg Leu Asn Thr Gln Gly Ala Ser Phe Asp Tyr Pro Val Ala
                500                 505                 510
Ser Asn Ala Thr Glu Gln Gly Arg Phe Gln Asn Arg Arg Ile Glu
                515                 520                 525
Phe Val Leu Phe Gln Glu Gly Glu Ala Ile Thr Gln Val Gly His
                530                 535                 540
Ala Glu Asp Ala Pro Thr Pro Val Ala Gln Asn
                545                 550 551

<210> SEQ ID NO 7
<211> LENGTH: 22
<212> TYPE: DNA
<213> ORGANISM: Moraxella catarrhalis
<220> FEATURE:
<222> LOCATION:
<223> OTHER INFORMATION: Pr 406

<400> SEQUENCE: 7
caaaagaaga caaacaagcagc                                              22

<210> SEQ ID NO 8
<211> LENGTH: 25
<212> TYPE: DNA
<213> ORGANISM: Moraxella catarrhalis
<220> FEATURE:
<222> LOCATION:
```

```
<223> OTHER INFORMATION: pr 408

<400> SEQUENCE: 8
cccatttagt atcagaagat gacac                                              25

<210> SEQ ID NO 9
<211> LENGTH: 21
<212> TYPE: DNA
<213> ORGANISM: Moraxella catarrhalis
<220> FEATURE:
<223> OTHER INFORMATION: pr 649

<400> SEQUENCE: 9
atcctgctcc aactgacttt c                                                  21

<210> SEQ ID NO 10
<211> LENGTH: 20
<212> TYPE: DNA
<213> ORGANISM: Moraxella catarrhalis
<220> FEATURE:
<223> OTHER INFORMATION: pr 650

<400> SEQUENCE: 10
ggtaacagaa cgctcaaccc                                                    20

<210> SEQ ID NO 11
<211> LENGTH: 19
<212> TYPE: DNA
<213> ORGANISM: Moraxella catarrhalis
<220> FEATURE:
<223> OTHER INFORMATION: pr 750

<400> SEQUENCE: 11
ccaaggggct gatttgaca                                                     19

<210> SEQ ID NO 12
<211> LENGTH: 20
<212> TYPE: DNA
<213> ORGANISM: Moraxella catarrhalis
<220> FEATURE:
<223> OTHER INFORMATION: pr 751

<400> SEQUENCE: 12
actatcagta accaggtttt                                                    20

<210> SEQ ID NO 13
<211> LENGTH: 20
<212> TYPE: DNA
<213> ORGANISM: Moraxella catarrhalis
<220> FEATURE:
<223> OTHER INFORMATION: pr 605

<400> SEQUENCE: 13
tgattggtga taaaagtagg                                                    20

<210> SEQ ID NO 14
<211> LENGTH: 19
<212> TYPE: DNA
<213> ORGANISM: Moraxella catarrhalis
<220> FEATURE:
<223> OTHER INFORMATION: pr 606

<400> SEQUENCE: 14
tgttggcatc taagggtc                                                      19
```

<210> SEQ ID NO 15
<211> LENGTH: 5570
<212> TYPE: DNA
<213> ORGANISM: Moraxella catarrhalis
<220> FEATURE:
<223> OTHER INFORMATION: LOS gene cluster from 25238 (type A)

<400> SEQUENCE: 15

```
caaaagaaga caaacaagca gcggagagtt ttccgagtgt atcaccaatc cataatgcat      60
gaattatcgg taaattttgg ttgggataag acataataat atacctgttt ttgtactgaa     120
tgttgagcta ttatttaaag ccaagtgatg atggtttgca agatgattga attgtttttt     180
aaaaaatttc tgttaatata tgatgtaaat tatcatttgt caattttagg cttattgcac     240
tgctcattta tgaaaatatt acatgtttta ctcactcgca tgcccattcc accgaccaaa     300
tatggcggca cagaaagagt attatgggca ttgtatcaag ggcaaactgc cttggggcat     360
gaagttaaat ttttaaccaa gcatgacaat aagcaccctg atgctttggt gtttaatcct     420
aatattagcc ttgaaaaaca ggtggaaggt tgggcggaca tcattcattt tcattttta      480
tatcgtggtg agattacgac acctttttgtc tgcaccacac acaatcaaca aatcacacct     540
gctagctttc ctaaaaatac cattttttg ggaaaattac acgcccagag aagtggtggg      600
caagcgtatg ttcataatgg gctgtattgg gcagattatg gtcagccgaa tttaaatatg      660
ccaaaaaatt atgtacattt tttggcaaat gcgaagtata agataaaaa tctcaaagat       720
agtgttacca tcgcccgtca agcaggcaga ccgttacatg ttatcggcag taaacgctac      780
tctttaaaat ataaagcagg caagtatcaa ccttattatt accaagggc tgatttgaca       840
ttttatggta tgcttggtgg ggataaaaaa aatgaggtca ttaaaaattc aagtgcattg      900
cttttttccag tacttaatta tgaagcgttt gggcttgcga tgattgaaag cttatatttg      960
ggctgtcctg tcattggcag tcggtgtggt tcattgccag agctgattat cccagaggtg     1020
ggcattagca cccaaagcaa atcagagatg gtagaggcaa tcaaaaacat cgccatattt     1080
aatcgtaagc attgccatga atacgctcaa gataacttta tcatttggt catgagtcaa      1140
aattatcttc actattatga taaagtactc aatggtgagt cgctacatga ccaagaacca     1200
agcgtaacac agaatctacc cacccaattt catttggtgg cttgaccatg aaaattttac     1260
atgtattatt aacttcattg ccgataccac cgaatgatta tggcggtaca gaaagagtat     1320
tatgggcatt gtatcaaggg caaactgcct tggggcatca ggtgcgtttt ttactcaaag     1380
ccaatgccaa tcatgcacct tatgtgcagg ttttttgatga gtcaaagcca ttacatgagc     1440
aaattgatga ctgggcggat atggtacatt ttcactttcc ttatgaaggt gagttacata     1500
aacctttttgt ttgcacagag cacagtaaca gtgaagttga aaaagagttt ccaatcaaca     1560
ccatttatct gtcttctaaa catgccgaaa ataatcacgc aacttgttat gtgcataatg     1620
gattatactg gcctgattat ggcgagccaa atttttaagcc aaaagattac tgccatttt      1680
tagccaaagc atcttggcgt attaagaact acaaggtgc tgtacgcatt gcaaaaaaag      1740
caaacaaacc attgcatatt tgggggggca atcgctttaa tatccgtcgc aatccctatt     1800
gttatttatc ttcacggttg catttcatg gaatggttgg cggagtaaag aaaaatgagc      1860
taattgccaa ctcacaagcg ttaatctttc ctgtgttgtg gcatgagcct tttgggcttg     1920
cagtcattga aagcctatat ttgggctgcc ctgtatttgc cacacctttt ggggcaatgc     1980
ctgatgttgt tacccaagaa gtggggcttt tgtcagacag ttatgcggtt ttaagtgaag     2040
cccttaaaga tgtggcacaa tttgaccgcc ttgcgtgcca tgaacatgct aagagacatt     2100
```

```
ttagtcattt gtctatgtca aacgcttatt tagactgtta tgaaaaagtt ttggcaggtg    2160
agagcctaaa cccatcacga cccatttcaa aatcaaatat taaagctcgt caaaaaatgt    2220
cagatgaata aaattttatg gtcattaatt aatcagcgaa atgcgacagt aatataaaaa    2280
aatcgttttc caaaacttct ataaaagcgt ttgactatct tgttgagttt ggtgtatagc    2340
gattcgttgg catgataaat atactggtga ttttttctat cctgctccaa ctgactttct    2400 agattttta tctgactgtc tgactgctgg cacagtgcag gcataactg tagtactttg     2460 cccttagaga gataagcacc aaacatgaca tggtcaatgg cataatattc atattcatca    2520
atacttttaa taaattctag tagccgctta gcacctgact ggctgataat atagccagcg    2580
gtgccgacat gggtgctttt tagagggttg agcgttctgt taccatggtg atggatactt    2640
ttgccaatat gaaccaattc atgctgagtt tcaagtttta taatatcaaa ctcaaaatat    2700
agccaatcat ttttaataaa acaagctgca tcattcccca aatagacatc gtcctcaaaa    2760
attgccatat aatccaagtt ttcatcaatc atctgttgcc atagtgctac atggcttaaa    2820
aagcaggctt tttcgccatc ggtgagtctt tggttgttga tgattgggat tgaaagcttt    2880
tgggcatact tgctaaatatc agtgggtgtt actgcatcaa aaaactcaaa ggcaatgcct    2940
tgtttgccaa attcacacat aatatgttct cttcttttg tggcagtttt tatgctgatg     3000
acaaaatttt gtatcatggt ttctccttat tgttaacca ccatagtatg atatatttat    3060
ctagggtata gcccatcgat gccatggcaa gaatatagcc ataagcacca cccaataagt    3120
cgccacgaat gacatactct cggataaaag aaaataccgc ccgaaaaaaa ccagcgatga    3180
gtgatgtgtt tttgttgtgg gtgaatttat cttttgccca atcgtaacta tatcggatat    3240
tttttaataa aaaatgatgc aaattgtcgt tggttaaatg tttaagataa ccatctaata    3300
ccatgcttgg cttgccatat tgattgagtg attcgtggac ttttaaatca gaatattgaa    3360
aatgttggcg tgcataaagt cgtgatagtt tgtcggcata ccaccagcgt ggttgtatct    3420
caatgccaca aaaggtatta actcgtgcca cactaaatac tttatcggtt tgcacaggat    3480
ttttgagtac atcggtaatg gcttgtcgca agggttggtc aaggcgttca tccgcatcaa    3540
gcgcaagcac ataatcgcct gtggcataag cttgggcaag ctgtcgctgt ttgccaaaac    3600
cttgccaatc ggtattgaca tgccatttg ccccataact tttggcgatt tggcgagtgt    3660
tatcagtact gccactgtct aacacaatga tttcatcaac gatatcatgc accgtctcta    3720
gacatgcttt tagatgttta ctttcgtttt tacaaatcat caccaatgac agcgtggatt    3780 tttttttgtga gacattaatg ggttttaagt tttgtgccat cgccaccgaa tgtaaaaaag    3840
cgtgttcggc ttggttgtgg gttaaatcat acagacaggc atatttatta aatgtatatt    3900
gggtaaaaaa taatgaataa atcagcccat aacgaccttg taagaatcga ccgtcaagta    3960
ggtattgttt aataaatgcc cataaaggat taaccacaac tttataaaac ttgcccttt     4020 tgccttgagc gtgcctgtca tctgcccatg ctttggcata atctaagcgt ttatttagcc    4080
aaaacagtgg cgtgggggcg gtgtggtggt gtaaaaaacc acttaatttt tggttgttg     4140 cgtcatttaa tatcacagat tcatgcacta ggttgttgtc atattgaaac tttttgggat    4200
acagtcgcca atgggcctta accccccata aggcattatc aatttgatgc ccaaagacaa    4260
aatcaagccg tttgatgcca taaaccgtat cggtagggg gttttgatg accttcaaaa      4320 tgctgttttt gagctgtggt gtcaccactt catcagcgtc caatgccaaa atccagtcgc    4380
ctgtggcata agcttgggca agctgtcgct gcctgccaaa gccttgccaa tcggtattga    4440
catgccattt tgccccatga ctttgggcaa ttttttgacc atcatcggtg ctgccactgt    4500
```

```
ctaaaatgat gatttcatct acccaatcgg caatggcagg caaagaaacc ttaagattgt    4560
cagcttcgtt tttgacaatc atcacgacag ataatcggta ccgcttggct gtattcatga    4620
taataagctt agaaaatggg ttgaagatga acattgaac  aatgggaatt tattttactt    4680
aactttaagt tgcttttcca gttattttaa acctagccaa aaatataatt tctaggtaca    4740
atagcgacaa gcaatcatgg caacatgaat gatcatttaa tcacggtatt aaaatttaat    4800
gaaactcatc tttttttgcaa atgttgtatt tatcatggtc atgttggtgg cttgtggtga   4860
tgaacctgct gtatcaacat cagccaagac agcaacaaca gatcccaaac aagactttta    4920
tatcggctgc tataccattg acaaaaatac gcctgccagt attaagatca gtcaagcaca    4980
aggcggctac aagatgcaaa tgaagaacc  aaacgatgcc gccaaaactt gggatacgcc    5040
agagccactg cttgtactca ccaaacaaga tggctggaag tattttttcta ccaatgccat    5100
caatttatca gtcaatgata tcaccgatca ggttatcgta agacctgacg ggctattggt    5160
tatcgctaag ctgcatgatg ccagtacgaa caccaatccc atgcttgata gtcgctatgc    5220
tgttgcctta atgggtgcgg taaataccat ctaccaagtc gcttgtgatg ataaacgcat    5280
taatttaata caagcgtttt aacataacca atcactgatt tgggcttaag tactaaaggg    5340
taaggaaaaa tggtatggga ttttttaggtt atttgttgat gggtggcatt gtttatacca    5400
ttggtttttt tattaatctt aaacgattac accccaagcg tcaggcgggt gcggtcattt    5460
gtgtcacaca cccaatcatg attggttatt tgctgggatg tttatgatt  atgcttggtg    5520
tgtcggtatt gcttgggcga tttgtattac atcatgatgg gccagattgg              5570
```

<210> SEQ ID NO 16
<211> LENGTH: 4583
<212> TYPE: DNA
<213> ORGANISM: Moraxella catarrhalis
<220> FEATURE:
<223> OTHER INFORMATION: LOS gene cluster from strain 7169 (type B)

<400> SEQUENCE: 16

```
caaaagaaga caaacaagca gcggagagtt ttccgagtgt atcaccaatc cataatgcat     60
gaattatcgg taaattttgg ttgggataag acataataat atatctgttt ttgtactgaa    120
tgttgagcta ttatttaaag ccaagtgatg atggtttgca agatgattga attgtttttt    180
taaaaaattt ctgttaatat atgatgtaaa ttatcatttg tcaattttag gcttattgca    240
ctgctcattt atgaaaatat tacatgtttt actcactcgc atgcccattc caccgaccaa    300
atatggcggc acagaaagag tattatgggc attgtatcaa gggcaaactg ccttggggca    360
tcaggtgcgt tttttactca aagccaatgc caatcatgca ccttatgtgc aggtttttga    420
taagtcaaag ccattacatg agcaaattga tgactgggcg gatatggtgc attttcactt    480
tccttatgaa ggtgagttac ataaaccttt tgtttgcaca gaacacagta acagtgaagt    540
tgaaaaagag tttccaatca acaccattta tctgtcttct aaacatgccg aaaataatca    600
cgcaacttgt tatgtgcata atggattata ctggcctgat tatggcgagc caaattttaa    660
gccaaaagat tactgccatt ttttagccaa agcatcttgg cgtattaaga acttacaagg    720
tgctgtacgc attgcaaaaa aagcaaacaa accattgcat attttggggg gcaatcgctt    780
taatatccgt cgcaatccct attgttattt atcttcacgg ttgcattttc atggaatggt    840
tggcggagta aagaaaaatg agctaattgc caactcacaa gcgttaatct ttcctgtgtt    900
gtggcatgag ccttttgggc ttgcagtcat tgaaagccta tatttgggct gtcctgtgtt    960
```

-continued

```
tgccacacct tttggggcaa tgtccgatat tgttacccaa gaagtggggc ttttgtcaga    1020
cagttatgcg gttttaagtg aagcccttaa agatgtggca caatttgacc gccttgcgtg    1080
ccatgaacat gctaagagac attttagtca tttgtctatg tcaaacgctt atttagactg    1140
ttatgaaaaa gttttggcag gtgagacttt aaatgcagtc aaaccaaaag caaagcctga    1200
tattaaagca agacagatga tgcaagatgg ttgatttaaa gaaaacctgg ttactgatag    1260
taagcttggt tactgaaaag cgattctttg aaaaaaagta cgcttaccaa tgcttcgata    1320
gtattttttg ccataatcag ctaaagtgcg tcttcgatgc tgattaacat tttgctttct    1380
ttgagtttct atcaaacttt taaatgtgtc atcttctgat actaaatggg cttgaatgac    1440
catggcagga ttgacttgta agacgctcat cttactaatg atggcatcaa aaatcacatg    1500
gtcaattgga aaaaattcaa aagcatctag tgttgataaa taatcaagta ttattttgc     1560 accttgttga gaaatgacat aacctgcagt gcctgtatga aaagttttta atgggcaaag    1620
ctgtcgatga ttaagaacag taacggcttt ttttatgtgt attttttcca cccaagtttc    1680
aagtttaatg acatcaacgg cattttgttg tagccaaatt gtcagttctt gtaagaattg    1740
ttgagagtca ttccccaaat agacatcgtc ctcaaaaatt gccatataat ccaagttttc    1800
atcaatcatc tgttgccata gtgctacatg gcttaaaaag caggcttttt cgccatcggt    1860
gagtctttgg ttgttggtga ttgggattga aagcttttgg gcgtacttgc taatatcagt    1920
gggtgttact gcatcaaaaa actcaaaggc aatgccttgt ttgccaaatt cacacataat    1980
atgttctctt cttttttgtgg cagttttttac actgatgaca aaattttgta tcatggttta    2040
tccttattat ttaaccacca tagcatgata tatttatcta gggtatagcc catcgatgcc    2100
atggcaagaa tatagccata agcaccaccc aataagtcgc cacgaatgac atactctcgg    2160
ataaaagaaa ataccgcccg aaaaaaacca gcgatgagtg atgtgttttt gttgtgggtg    2220
aatttatctt ttgcccaatc gtaactatat cggatatttt ttaataaaaa atgatgcaaa    2280
ttgtcgttgg ttaaatgttt aagataacca tctaatacca tgcttggctt gccatattga    2340
ttgagtgatt cgtggacttt taaatcagaa tattgaaaat gttggcgtgc ataaagtcgt    2400
gatagtttgt cggcatacca ccagcgtggt tgtacctcaa tgccacaaaa ggtattaact    2460
cgtgccacac taaatacttt atcggtttgc acaggatttt tgagtacatc ggtaatggct    2520
tgtcgcaagg gttggtcaag gcgttcatcc gcatcaagca caagcacata atcgcctgtg    2580
gcataagctt gggcaagctg tcgctgtttg ccaaagcctt gccaatcggt attgacatgc    2640
cattttgccc cataactttc ggcgatttgg cgagtgttat cagtactgcc actgtctaac    2700
acaatgattt catcaacaat atcatgcacc gtctctagac atgcttttag atgtttactt    2760
tcatttttac aaatcatcac caatgacagc gtggattttt tttgtgagac attaatgggt    2820
tttaagtttt gtgccatcgc caccgaatgt aaaaaagcgt gttcggcttg gttgtgggtt    2880
aaatcataca gacaggcata tttattaaat gtatattggg taaaaaataa tgaataaatc    2940
agcccataac gaccttgtaa gaatcgaccg tcaagtaggt attgtttaat aaatgcccat    3000
aaaggattaa ccacaacttt ataaaacttg ccctttttgc cttgagcgtg cctgtcatct    3060
gcccatgctt tggcataatc taagcgttta tttagccaaa acagtggcgt gggggcggtg    3120
tggtggtgta aaaaaccact taattttttg gttgttgcgt catttaatat cacagattca    3180
tgcactaggt tgttgtcata ttgaaacttt ttgggataca gtcgccaatg ggccttaacc    3240
ccccataagg cattatcaat ttgatgccca aagacaaaat caagccgttt gatgccataa    3300
accgtatcgg tagggggggtt tttgatgacc tttaaaatgc tgtttttgag ctgtggtgtc    3360
```

```
accacttcat cagcgtccaa tgccaaaatc cagtcgcctg tggcataagc ttgggcaagc    3420
tgtcgctgcc tgccaaagcc ttgccaatcg gtattgacat gccattttgc cccatgactt    3480
tgggcaattt tttgaccatc atcggtgctg ccactgtcta aaatgatgat ttcatctacc    3540
caatcggcaa tggcaggcaa agaaaccttq agattgtcag cttcgttttt gacaatcatc    3600
acgacagata atcggtaccg cttggctgta ttcatgataa taagcttaga aaatgggttg    3660
aagatgaaac attgaacaat gggaagttat tttacttaac tttaagttgc ttttccagtt    3720
attttaaacc tagccaaaaa tataatttct aggtacaata gcgacaagca atcatggcaa    3780
catgaatgat catttaatca cggtattaaa atttaatgaa actcatcttt tttgcaaatg    3840
ttgtatttat catggtcatg ttggtggctt gtggtgatga acctgctgta tcaacatcag    3900
ccaagacagc aacaacagat cccaaacaag acttttatat cggctgctat accattgaca    3960
aaaatacgcc tgccagtatt aagatcagtc aagcacaagg cggctacaag atgcaaatga    4020 agaaccaaa cgatgccgcc aaagcttggg ataccagc gccactgctt gtactcacca    4080
aacaagatgg ctggaagtat ttttctacca atgccatcaa tttatcagtc aatgatatca    4140
ccgatcaggt tatcgtaaga cctgacgggc tattggttat cgctaagctg catgatgcca    4200
gtacgaacac caatcccatg cttgatagtc gctatgctgt tgccttaatg ggtgcggtaa    4260
ataccatcta ccaagtcgct tgtgatgata aacgcattaa tttaatacaa gcgttttaac    4320
ataaccaatc actgatttgg gcttaagtac taaagggtaa ggaaaaatgg tatgggattt    4380
ttaggttatt tgttgatggg tggcattgtt tataccattg gttttttttat taatcttaaa    4440 cgattacacc ccaagcgtca ggcgggtgcg gtcatttgtg tcacacaccc aatcatgatt    4500
ggttatttgc tgggatgttt tatgattatg cttggtgtgt cggtattgct tgggcgattt    4560
gtattacatc atgatgggcc aga                                            4583
```

<210> SEQ ID NO 17
<211> LENGTH: 5584
<212> TYPE: DNA
<213> ORGANISM: Moraxella catarrhalis
<220> FEATURE:
<223> OTHER INFORMATION: LOS gene cluster from RS-10 (type C)

<400> SEQUENCE: 17

```
caaaagaaga caaacaagca gcggagagtt ttccgagtgt atcaccaatc cataatgcat      60
gaattatcgg taaattttgg ttgggataag acataataat atacctgttt ttgtactgaa     120
tgttgagcta ttatttaaag ccaagtgatg atggtttgca agatgattga attgtttttt     180
aaaaaatttc tgttaatata tgatgtaaat tatcatttgt caattttagg cttattgcac     240
tgctcattta tgaaaatatt acatgttttt a ctcactcgca tgcccattcc accgaccaaa    300
tatgcgggca cagaaagagt attatgggca ttgtatcaag gcaaactgc cttggggcat     360 gaagttaaat ttttaaccaa gcatgacaat aagcaccctg atgctttggt gtttaatcct     420
aatatcagcc ttgaaaaaca ggtggaaggt tgggcggaca tcattcattt tcattttttta    480 tatcgtggtg agattacgac accttttgtc tgcaccacac acaatcaaca aatcacacct     540
gccagctttc ccaaaaatac catttttttttg ggaaaattac acgcccagag aagcggtggt    600
caagcgtatg ttcataatgg gctgtattgg gcagattatg ccagccgaa tttaaatacg     660 ccaaaaaatt atgtacattt tttgcaaat gcgaagtata aagataaaaa tctcaaagat    720
agtgttacca tcgcccgtca agcaggcaga ccgttacatg ttatcggcag taaacgctac    780
```

```
tctttaaaat ataaagcagg caagtatcaa ccttattatt accaaggggc tgatttgaca    840
ttttatggta tgcttggtgg ggataaaaaa aatgaggtca ttaaaaattc aagtgcattg    900 cttttttccag tacttaatta tgaagcgttt gggcttgcga tgattgaaag cttatatttg   960
ggctgtcctg tcattggcag tcggtgtggt tcattgccag agctgattat cccagaggtg   1020
ggcattagca cccaaaagcaa atcagagatg gtagaggcaa tcaaaaacat cgccatattt   1080
aatcgtaagc attgccatga atacgctcaa gataacttta tcatttggt catgagtcaa    1140 aattatcttc actattatga taaagtactc aatggtgagt cgctacatga ccaagaacca   1200
agcgtaacac agaatctacc cacccaattt catttggtgg cttgaccatg aaaattttac   1260
atgtattatt aacttcattg ccgataccac cgaatgatta tggcggtaca gaaagagtat   1320
tatgggcatt gtatcaaggg caaactgcct tggggcatca ggtgcgtttt ttactcaaag   1380
ccaatgccaa tcatgcacct tatgtgcagg ttttgatga gtcaaagcca ttacatgagc   1440
aaattgatga ctgggcggat atggtacatt ttcactttcc ttatgaaggt gagttacata   1500
aaccttttgt ttgcacagag cacagtaaca gtgaagttga aaagagttt ccaatcaaca    1560 ccatttatct gtcttctaaa catgccgaaa ataatcacgc aacttgttat gtgcataatg   1620
gattatactg gcctgattat ggcgagccaa attttaagcc aaaagattac tgccattttt   1680
tagccaaagc atcttggcgt attaagaact acaaggtgc tgtacgcatt gcaaaaaaag   1740
caaacaaacc attgcatatt tgggggggca atcgctttaa tatccgtcgc aatccctatt   1800
gttatttatc ttcacggttg cattttcatg gaatggttgg cggagtaaag aaaaatgagc   1860
taattgccaa ctcacaagca ttaatctttc ctgtgttgtg gcatgagcct tttgggcttg   1920
cagtcattga aagcctatat ttgggctgtc ctgtgttttgc cacaccttt ggggcaatgt    1980 ccgatattgt tacccaagaa gtggggcttt tgtcagatag ttatgcggtt ttaagtgaag   2040
cccttaaaga tgtggcacaa tttgaccgcc ttgcgtgcca tgaacatgct aagagacatt   2100
ttagtcattt gtctatgtca aacgcttatt tagactgtta tgaaaaagtt ttggcaggtg   2160
agactttaaa tgcagtcaaa ccaaaagcaa agcctgatat taaagcaaga cagatgatgc   2220
aagatggttg atttaaagaa aacctggtta ctgatagtaa gcttggttac tgaaaagcga   2280
ttctttgaaa aaagtacgc ttaccaatgc ttcgatagta ttttttgcca taatcagcta    2340
aagtgcgtct tcgatgctga ttaacatttt gctttctttg agtttctatc aaacttttaa   2400
atgtgtcatc ttctgatact aaatgggctt gaatgaccat ggcaggattg acttgtaaga   2460
cgctcatctt actaatgatg gcatcaaaaa tcacatggtc aattggaaaa aattcaaaag   2520
catctagtgt tgataaataa tcaagtatta tttttgcacc ttgttgagaa atgacataac   2580
ctgcagtgcc tgtatgaaaa gtttttaatg ggcaaagctg tcgatgatta agaacagtaa   2640
cggctttttt tatgtgtatt ttttccaccc aagtttcaag tttaatgaca tcaacggcat   2700
tttgttgtag ccaaattgtc agttcttgta agaattgttg agagtcattc cccaaataga   2760
catcgtcctc aaaaattgcc atataatcca gtttcatc aatcatctgt gccatagtg     2820 ctacatggct taaaaagcag gctttttcgc catcggtgag tctttggttg ttgatgattg   2880
ggattgaaag cttttgggcg tacttgctaa tatcagtggg tgttactgca tcaaaaaact   2940
caaaggcaat gccttgtttg ccaaattcac acataatatg ttctcttctt tttgtggcag   3000
tttttacact gatgacaaaa ttttgtatca tggtttatcc ttattgttta accaccatag   3060
catgatatat ttatctaggg tatagcccat cgatgccatg gcaagaatat agccataagc   3120
accacccaat aagtcgccac gaatgacata ctctcggata aagaaaata ccgcccgaaa    3180
```

```
aaaaccagcg atgagtgatg tgttttgtt gtgggtgaat ttatcttttg cccaatcgtc    3240
actatagcgg atatttttta ataaaaatg atgcaaattg tcgttggtca aatgcttaag    3300
ataaccatct aataccatgc ttggcttgcc atattgattg agtgattcgt ggactttaa    3360
atcagaatat tgaaaatgtt ggcgtgcata aagtcgtgat agcttatcgg tataccacca    3420
gcgtggttgt acctcaatgc cacaaaaggt attaactcgt gccacactaa atactttatc    3480
ggtttgcaca ggattttga gcacatcggt aatggcttgt cgcaagggtt ggtcaaggcg    3540
ttcatccgca tcaagcacaa gcacataatc gcctgtggca taagcttggg caagctgtcg    3600
ctgtttgcca aagccttgcc aatcggtatt gacatgccat tttgccccat aactttcggc    3660
gatttggcga gtgttatcag tactgccact gtcaacaca atgatttcat caacgatatc    3720
atgcaccgtc tctagacatg cttttagatg tttactttca tttttacaaa tcatcaccaa    3780
tgacagcgtg gattttttt gtgagacatt aatgggtttt aagttttgtg ccatcgccac    3840
cgaatgtaaa aaagcgtgtt cggcttggtt gtgggttaaa tcatacagac aggcatattt    3900
attaaatgta tattgggtaa aaataatga ataaatcagc ccataacgac cttgtaagaa    3960
tcgaccgtca agtaggtatt gtttaataaa tgcccataaa ggattaacca caactttata    4020
aaacttgccc tttttgcctt gagcgtgcct gtcatctgcc catgctttgg cataatctaa    4080
gcgtttattt agccaaaaca gcggcgtggg ggcggtgtgg tggtgtaaaa aaccacttaa    4140
tttttttggtt gttgcgtcat ttaatatcac agattcatgc actaggttgt tgtcatattg    4200
aaacttttg ggatacagtc gccaatgggc cttaacccc cataaggcat tatcaatttg    4260
atgcccaaag acaaaatcaa gccgtttgat gccataaacc gtatcggtag gggggttttt    4320
gatgaccttt aaaatgctgt ttttgagctg tggcgttacc acttcatcag cgtccaatgc    4380
caaaatccag tcgcctgtgg cataagcttg ggcaagctgt cgctgcctgc caaagccttg    4440
ccaatcggta ttaacatgcc attttgcccc atgactttgg gcaattttt gaccatcatc    4500
ggtactgcca ctgtctaaaa tgatgatttc atctacccaa tcggcaatgg caggcaaaga    4560
aaccttaaga ttgtcagctt cgttttgac aatcatcacg acagataatc ggtaccgctt    4620
ggctgtattc atgataataa gcttagaaaa tgggttgaag atgaaacatt gaacaatggg    4680
aagttatttt acttaacttt aagttgcttt tccagttatt ttaaacctag ccaaaaatat    4740
aatttctagg tacaatagcg acaagcaatc atggcaacat gaatgatcat ttaatcacgg    4800
tattaaaatt taatgaaact catcttttt gcaaatgttg tatttatcat ggtcatgttg    4860
gtggcttgtg gtgatgaacc tgctgtatca acatcagcca agacagcaac aacagatccc    4920
aaacaagact tttatatcgg ctgctatacc attgacaaaa atacgcctgc cagtattaag    4980
atcagtcaag cacaaggcgg ctacaagatg caaatgaaag aaccaaacga tgccgccaaa    5040
acttgggata caccagagcc actgcttgta ctcaccaaac aagatggctg gaagtatttt    5100
tctaccaatg ccatcaattt atcagtcaat gatatcaccg atcaggttat cgtaagacct    5160
gacgggctat tggttatcgc taagctgcat gatgccagta cgaacaccaa tcccatgctt    5220
gatagtcgct atgctgttgc cttaatgggt gcggtaaata ccatctacca agtcgcttgt    5280
gatgataaac gcattaattt aatacaagcg ttttaacata accaatcact gatttgggct    5340
taagtactaa agggtaagga aaaatggtat gggattttta ggttatttgt tgatgggtgg    5400
cattgtttat accattggtt tttttattaa tcttaaacga ttacaccca agcgtcaggc    5460
```

```
gggtgcggtc atttgtgtca cacacccaat catgattggt tatttgctgg gatgttttat    5520
gattatgctt ggtgtatcgg tattgcttgg gcgatttgta ttacatcatg atgggccgga    5580
tggc                                                                 5584
```

TOOLS FOR DETECTING *MORAXELLA CATARRHALIS*

This application claims the priority of U.S. Provisional Application Ser. No. 60/470,022, filed on May 13, 2003, the disclosure of which is incorporated herein by reference.

FIELD OF THE INVENTION

The present invention relates generally to the area of *Moraxella catarrhalis* infections and more particularly provides tools for specifically detecting *Moraxella catarrhalis*.

BACKGROUND OF THE INVENTION

*Moraxella catarrhalis* is a Gram-negative *diplococcus* that primarily infects young children where it is a major cause of bacteria-induced acute otitis media (AOM). Older adults with underlying lung disease such as chronic obstructive pulmonary disease (COPD) are also frequently affected. More than 3.5 million cases of AOM are recorded every year in the United States, and it is estimated that 80% of children have experienced at least one episode of otitis before reaching the age of 3 (Klein, J O (1994) Clin. Inf. Dis 19:823). Left untreated the disease may lead to hearing loss. Most cases of AOM are caused by one of three major pathogens, *Streptococcus pneumoniae* (*S. pneumoniae*) (30-40%), non-typeable *Haemophilus influenzae* (NTHi) (30%) and *Moraxella catarrhalis* (*M. catarrhalis*) (20%).

The treatment of the estimated 24 million cases of childhood AOM that occur each year in the United States is the single most prominent reason for prescribing0 antibiotics (Teele, et al 2001. Vaccine 19: S140-S143). In the past three decades, there has been a dramatic worldwide increase in antibiotic resistance in AOM pathogens which has resulted in a reduction of the number of effective antibiotics for this disease and has begun to pose a major public health threat. Accordingly, there is a need for reliable and rapid methods for identifying *Moraxella catarrhalis* infections in AOM. Further, there is a need for reliable and rapid methods by which *Moraxella catarrhalis* can be distinguished from other strains of *Moraxella* and other infectious organisms known to cause AOM., as *M. catarrhalis* induced AOM can not be diagnosed based on symptomology alone unlike other AOM pathogens.

SUMMARY OF THE INVENTION

The present invention provides compositions and methods useful for detecting *Moraxella catarrhalis*. The compositions are antibodies, proteins or nucleic acid sequences specific to *Moraxella catarrhalis* (*M. catarrhalis*).

The method comprises the steps of obtaining a biological sample from an individual and detecting within the biological sample the presence of proteins, nucleic acid sequences and lipooligosaccharides (LOS) specific to *Moraxella catarrhalis*. Further, compositions and methods useful for distinguishing between *M. catarrhalis* serotypes are provided.

BRIEF DESCRIPTION OF THE FIGURES

FIG. 1B demonstrates reactivity of a monoclonal antibody (MAb) to all three *M. catarrhalis* serotypes. The lanes are: a-25238 serotype A, b-CCUG 3292 serotype B, c-RS-10 serotype C, d-RS-26 serotype C, e-7169 (strain "B" from Buffalo (child), f-7431 isolate from Ohio (child), g-sk633 isolate from Buffalo (adult), h-O35E isolate from Houston (child), i-Tal 1 isolate from Philadelphia (adult), j-7482 isolate from Japan (child), k-7418 isolate from France (adult), l-7512 isolate from Belgium (child).

FIG. 1B demonstrates that MAb 4G5 reacts all three the *M. catarrhalis* LOS A, B and C serotypes.

DETAILED DESCRIPTION OF THE INVENTION

Figure 1A:
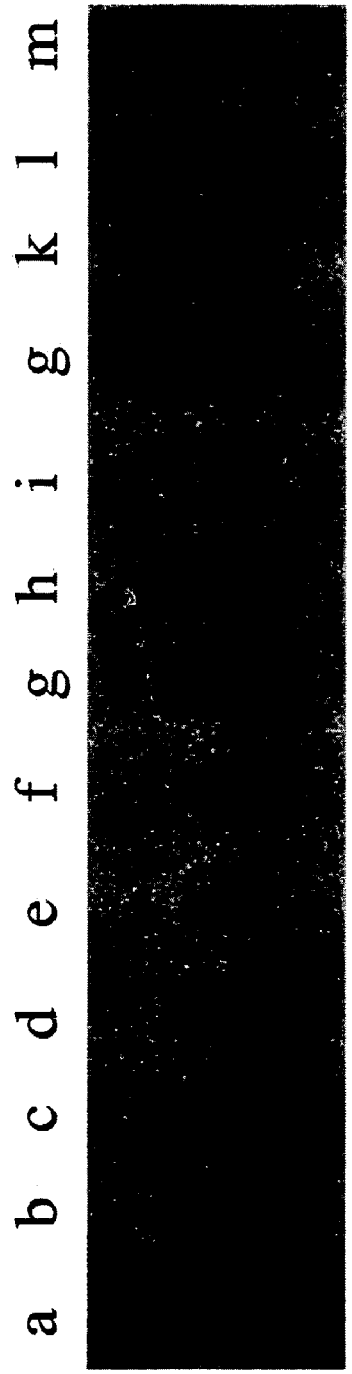
FIGS. 1A and 1B are representations of an SDS PAGE gel and Western blot of the gel, respectively.

The present invention provides compositions and methods useful for detecting *Moraxella catarrhalis*. The compositions provided are antibodies, proteins or nucleic acid sequences unique to *M. catarrhalis*.

The method comprises the steps of obtaining a biological sample from an individual and detecting in the biological sample the presence of proteins, nucleic acid sequences, lipooligosaccharides (LOS) or antigens specific to *Moraxella catarrhalis*. The compositions and methods provided are therefore useful not only for detecting *M. catarrhalis* in a biological sample, but also for distinguishing *M. catarrhalis* from other organisms which may be present in the sample, and for further distinguishing between *M. catarrhalis* serotypes as will be described more fully below.

Biological Samples

A "biological sample" as used herein refers to a sample, such as tissue or fluid obtained from an individual, including without limitation urine, plasma, serum, lymph, tears, saliva, sputum, mucous, mucosal swabs, inner ear swabs and tissue sections.

Methods for obtaining biological samples are well known to those skilled in the art. For example, suitable biological samples can be obtained by swabbing mucosal surfaces such as the nasal cavity, oropharynx or throat area, inner ear swabs, sputum samples urine, blood and/or plasma samples using well known collection techniques.

Immunoassays

Once the biological sample is obtained, it can be prepared for immunological detection of *M. catarrhalis* by a wide variety of immunoassays using the MAbs of the present invention which are specific for *Moraxella catarrhalis*. By describing proteins, nucleic acid sequences lipooligosaccharides and antigens (LOS) as "specific to *Moraxella catarrhalis*" it is meant that the particular feature so described is unique to *Moraxella catarrhalis* and is not found in other tested organisms.

Procedures for preparing biological samples for and performing Westerns blots, enzyme-linked immunosorbent assays (ELISA), radioimmunoassays (RIAs), capture assays and non-enzyme linked antibody binding assays are all well known.

In one embodiment, Western blots are performed with the MAbs of the present invention by separating whole cell lysates or outer membrane proteins by sodium dodecyl sulfate polyacrylamide gel electrophoresis (SDS-PAGE), after which the proteins are transferred to a suitable substrate such as nitrocellulose membrane by application of an electric field in a transfer buffer. The substrate is then incubated with a blocking buffer which allows for blocking of nonspecific adsorption sites on the immobilizing substrate and thus reduces the background caused by non-specific binding of antibodies onto the surface. The blot is then incubated with a primary antibody to induce specific immunocomplex formation and washed in a suitable washing buffer. The primary antibody may be one or a combination of the MAbs provided herein. The occurrence and amount of immunocomplex formation may be determined by subjecting the immunocomplex to a secondary antibody having specificity for the primary antibody. To provide means for detection, the second antibody may have an associated activity such as an enzymatic activity that will generate, for example, a color development upon incubating with an appropriate chromogenic substrate. Quantification may then be achieved by measuring the degree of color generation using any suitable means, such as a spectrophotometer.

In another embodiment, the MAbs of the present invention are used in ELISA assays to detect *M. catarrhalis* from a biological sample. In general, such an ELISA assay (Coligan et al., Current Protocols in Immunology 1(2), Chapter 6, (1991)) initially comprises providing an antibody specific to an *M. catarrhalis* antigen, preferably a monoclonal antibody. In addition, a secondary antibody is prepared against the monoclonal antibody. To the secondary antibody is attached a detectable reagent such as radioactivity, fluorescence or colorimetric reagent such as horseradish peroxidase enzyme. The biological sample is prepared using standard techniques and incubated on a solid support, e.g. a polystyrene dish, which binds the proteins in the sample. Any free protein binding sites on the dish are then covered by incubating with a non-specific protein, such as, bovine serum albumen.

Next, the monoclonal antibody is incubated in the dish during which time the monoclonal antibodies attach to any *M. catarrhalis* proteins attached to the polystyrene dish. All unbound monoclonal antibody is washed out with buffer. The secondary antibody linked to the detectable reagent is placed in the dish resulting in binding of the secondary antibody to any monoclonal antibody bound to *M. catarrhalis* proteins. Unattached secondary antibody is then washed out and any necessary reagents are then added to the dish and the amount of detectable reagent developed in a given time period is a measurement of the amount of *M. catarrhalis* protein present.

In another embodiment, the MAbs of the invention may be used in an immunochromatographic ("ICT") strip assay. A class of devices known as ICT devices uses immunoassay techniques in combination with a label that is conjugated with an antibody. Such devices are now commonly used for rapid, reliable field tests to determine the presence or absence of a particular analyte. The label, when attached to antibody/antigen molecules that are then amassed together in a specific, restricted area, becomes readily detectable by the naked human eye, or by a scanning device, depending on the type of label used. In general, the label can be a particle of latex, gold, or carbon, a radioactive particle, a magnetic particle, or have other physical or chemical properties that allow it to be fixed or attracted to a certain defined area. ICT devices that use the sandwich technique are particularly easy to use. With this technique, labeled antibody that binds with the specific antigen to be assayed is mixed with the sample that is suspected of containing the specific antigen. If the antigen is present in the sample, the labeled antibody binds with the antigen to form a label-antibody-antigen complex. A second antibody that is immovably fixed at a test zone and that also binds with the specific antigen binds the label-antibody-antigen complex at the test zone. A positive result is made visible by the accumulation of the label at the test zone. Such devices are economical and can be used by unskilled workers. Thus, a method that uses such an ICT device to determine, in a single assay, the presence or absence of multiple enteric pathogens, in particular, multiple enteric pathogens, plus a general marker for an inflammatory condition of the intestines would provide valuable diagnostic information to a treating physician.

Several types of such ICT devices are known. Most are the "dipstick" type in which a test strip is encased in a hollow housing with a bibulous pad extending from one end. This pad is dipped into the liquid sample and draws the liquid by capillary ("wicking") action up onto a section of the test strip that contains a labeled antibody, i.e., a label conjugated to an antibody that will specifically bind with the antigen being assayed. The labeled antibody moves with the liquid that is being drawn by the capillary action further along the test strip and, if the specific antigen to which the antibody binds is present in the liquid sample, the labeled antibody will bind with the antigen, forming a labeled antibody-antigen complex. This complex continues to flow with the liquid along the test strip. Downstream from the area containing the conjugated antibody is a test zone. This test zone is typically a nitrocellulose pad into which a second binding partner, an antibody that binds to the same antigen as the labeled antibody, but to a second epitope of the antigen, has been immovably fixed. The fixed antibody will attach to the labeled antibody-antigen complex that flows onto the test zone and will bind the complex to the test zone. The presence of an antigen being assayed is then visible as a stripe across the test zone or otherwise readily detectable. The excess liquid continues to flow past the test zone across a control zone. There are a number of well-known means in the field of immunoassay of creating a control zone, such as embedding into the control zone a binding partner that binds non-specifically to one or more of the labeled antibodies contained on the conjugate section, or to a labeled analyte added to the liquid sample for the purpose of binding with the non-specific binding partner at the control zone. A properly completed test will always show a visible stripe across the control zone or, if a radioisotope or magnetic particle is used as a label, an otherwise readily detectable stripe. Typically, for those devices using a colored label, the housing of the ICT device has a window through which to view the test zone and the control zone. Devices of this type have been disclosed in May et al. (U.S. Pat. No. 5,622,871; issued Apr. 22, 1997) and Charlton et al. (U.S. Pat. No. 5,714,389; issued Feb. 3, 1998).

Further, U.S. Pat. Nos. 5,869,345, 5,877,028, and 6,727,073 disclose ICT devices that are two-panel cards containing a test strip on one panel and a sample well on the other panel. These devices uses the sandwich technique described above with the dipstick devices, but have a particular advantage in that they allow the sample to be prepared for the test directly on the test card, rather than in a separate vessel. When the test card is closed, liquid from the sample well flows onto the test strip. As with the other devices, a window is provided through which to view the results.

Antibodies and Proteins

In various embodiments, the present invention provides antibodies that can bind surface and/or internal antigens specific to M. catarrhalis and are useful for detecting M. catarrhalis in the immunoassays as described above and as otherwise known in the art.

In one embodiment the present invention provides monoclonal antibodies (MAbs) to M. LOS antigens, which are the predominant, surface-exposed component of the M. catarrhalis outer membrane and have been implicated as a virulence factor in the pathogenesis of M. catarrhalis infections.

Three LOS serotypes (A, B and C) have been identified on the basis of structural and immunologic analyses of the LOS terminal oligosaccharide branch extensions. The A and B LOS serotypes of M. catarrhalis account for over 90%-95% of all M. catarrhalis isolates, and approximately 30% of isolates are serotype B.

In one embodiment of the invention, a MAb that can detect all three LOS serotypes is provided. In another embodiment, a MAb that is specific for a particular serotype is provided. For example, can discriminate the B serotype of M. catarrhalis is provided.

While providing MAbs to LOS antigens is useful for detection of M. catarrhalis, the present invention contemplates the use of combinations of antibodies to provide more complete detection of M. catarrhalis present in a biological sample. Accordingly, in yet another embodiment, the invention provides a novel MAb and novel M. catarrhalis surface protein to which the MAb is directed.

Further, detection of surface antigens may be combined with detection of internal antigens to improve detection of M. catarrhalis in a biological sample. The present invention therefore provides in another embodiment a novel MAb and novel internal M. catarrhalis internal protein to which the MAb is directed to.

Nucleic Acids

Biological samples can be prepared for detection of unique M. catarrhalis nucleic acids by a wide variety of well known techniques. For example, genomic DNA can be isolated from a biological sample using any suitable technique such as by various kits and reagents for isolation of genomic DNA which are available commercially, for example, those provided by Qiagen (Valencia, Calif.). Alternatively, genomic DNA can be isolated by standard alkaline lysis procedures followed by equilibrium ultracentrifugation in cesium chloride gradients or ethanol precipitation.

The nucleic acid molecules of the invention can be used to detect M. catarrhalis using various techniques such as PCR amplification or hybridization technologies such as Northern blotting or microarrays.

In one embodiment, DNA isolated from a biological sample is analyzed using PCR to detect the presence of M. catarrhalis DNA. PCR reactions can be carried out according to methods well known to those skilled in the art. For examples of suitable PCR protocols see Sambrook et al, "Molecular Cloning: A Laboratory Manual" Cold Spring Harbor Laboratory Press; 3rd edition (2001). Briefly, PCR is performed by subjecting isolated nucleic acids the following steps: denaturation of the nucleic acids, annealing primers to the nucleic acids, extension of the primers with polymerase, and repeating the cycle for as many repetitions as desired, with a typical number of cycles being about thirty.

Accordingly, in one embodiment, the invention provides nucleic acid sequences, the detection of which definitively indicates the presence of M. catarrhalis in a biological sample.

In another embodiment, sets of PCR primers that are useful for detecting M. catarrhalis in biological samples are provided. Further, the invention provides sets of primers that can be used to determine the specific LOS serotype of M. catarrhalis in a biological sample.

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitations.

EXAMPLE 1

This Example demonstrates a MAb that can recognize all three LOS serotypes of M. catarrhalis.

MAb 4G5 was developed by immunizing BALB/c mice using well known methods with iron-stressed whole bacteria of *M. catarrhalis* strain 25240. A fusion was performed after 28 days in which splenocytes from the immunized animals were fused to mouse myeloma cells. The resulting hybridomas were screened for the production of antibody by immunodot assay versus iron-stressed and iron-replete whole bacteria. All clones that were positive for the production of MAb to the crude antigen preparations were further tested in Western blots versus iron-stressed and iron-replete whole bacteria and subsequently against outer membrane proteins. This identified the target molecule as LOS for Mab 4G5. The hybridmoma that produces mAb 4G5 was deposited pursuant to the Budapest Treaty requirements with the American Type Culture Collection (ATCC), 10801 University Boulevard, Manassas, Va., 20110, on Jul. 18, 2007, and has been assianed Patent Deposit Designation PTA-8544.

Figure 1B:

FIGS. 1A and 1B are representations of an SDS PAGE gel and Western blot of the gel, respectively. FIG. 1B demonstrates reactivity of a monoclonal antibody (MAb) to all three *M. catarrhalis* serotypes. The lanes are: a-25238 serotype A, b-CCUG 3292 serotype B, c-RS-10 serotype C, d-RS-26 serotype C, e-7169 (strain "B" from Buffalo (child), f-7431 isolate from Ohio (child), g-sk633 isolate from Buffalo (adult), h-O35E isolate from Houston (child), i-Tal 1 isolate from Philadelphia (adult), j-7482 isolate from Japan (child), k-7418 isolate from France (adult), 1-7512 isolate from Belgium (child).

These data demonstrate that MAb 4G5 recognizes LOS conserved on a diversity of clinical isolates from different geographic regions, from both adults and children, and that MAb 4G5 recognizes the *M. catarrhalis* LOS A, B and C serotypes.

Further, additional Western blots assays with MAb 4G5 using proteinase K lysates from 8 strains of *H. influenzae*, 11 strains of *N. meningitidis*, 12 strains of *N. gonorrhoeae*, 2 strains of *Neisseria lactamica*, and 2 strains of *Neisseria cinerea* were performed, and none reacted with MAb 4G5. (Data not shown).

Thus, these data indicate that MAb 4G5 is specific for the LOS that is found on all three *M. catarrhalis* LOS serotypes. Further, these data demonstrate that MAb 4G5 distinguishes *M. catarrhalis* from pathogenic organisms that are found commensally with human biological mucus samples.

EXAMPLE 2

This Example demonstrates a MAb that can discriminate one of the three LOS serotypes.

MAb 3F7 (an IgM) is specific for *M. catarrhalis* LOS serotype B. Monoclonal antibodies 3F7 was developed essentially as described in Example 1 by immunizing mice with iron-stressed outer membranes proteins from *M. catarrhalis* strain 7169. Once reactivity was identified, further testing in Western blot versus iron-stressed and iron-replete whole bacteria was performed and subsequently outer membrane proteins which identified LOS B as the molecule targeted by Mab 3F7, as can be seen in FIG. 2.

Figure 2:
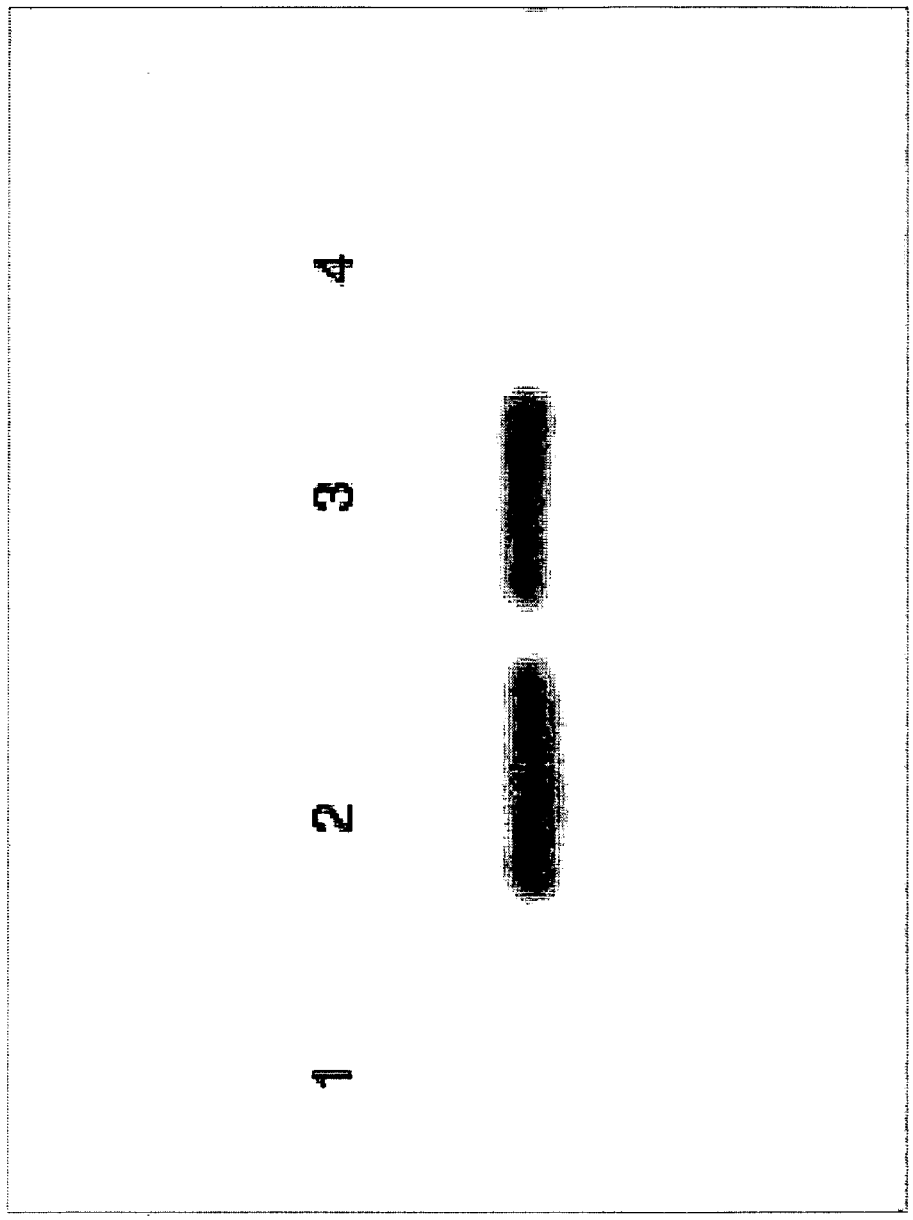
FIG. 2 is a representation of a Western blot probed with a MAb that recognizes the LOS B serotype of *M. catarrhalis*. The antibody with which the Western was probed is Mab 3F7. Lane 1 demonstrates a lack of reactivity between MAb 3F7 and strain 25238 (serotype A). Lane 2 demonstrates MAb 3F7 reacting with strain CCUG3292 (serotype B). Lane 3 demonstrates MAb 3F7 reacting with strain 7169 (serotype B), and lane 4 demonstrates a lack of reactivity between MAb 3F7 and strain RS-10 (serotype C).

FIG. 2 is a representation of a Western blot probed with a MAb that recognizes the LOS B serotype of *M. catarrhalis*. The antibody with which the Western was probed is Mab 3F7. Lane 1 demonstrates a lack of reactivity between MAb 3F7 and strain 25238 (serotype A). Lane 2 demonstrates MAb 3F7 reacting with strain CCUG3292 (serotype B). Lane 3 demonstrates MAb 3F7 reacting with strain 7169 (serotype B), and lane 4 demonstrates a lack of reactivity between MAb 3F7 and strain RS-10 (serotype C). Thus, MAb 3F7 recognizes only LOS B in lanes 2 and 3, and can therefore discriminate the LOS B serotype.

Further, MAb 3F7 was tested against non *M. catarrhalis* strains including 4 Nontypable *Haemophilus influenzae*, 3 *Neisseria gonorrhoeae* and 4 *Neisseria meningitidis*, all of which were negative for interaction with MAb 3F7 as confirmed by Western blotting.

These results therefore demonstrate that MAb 3F7 can discriminate the B LOS serotype of *M. catarrhalis* and is specific for *M. catarrhalis* versus other organisms.

EXAMPLE 3

This Example demonstrates a MAb specific for a novel surface protein unique to *M. catarrhalis*.

MAb 3F5-5E5 was developed as described in Example 1. MAb 3F5-5E5 is specific for the MhuA surface protein of *M. catarrhalis*. MhuA is a novel putative hemoglobin (Hb)-binding protein homologue gene, and that the gene represented by SEQ ID NO:1 encodes the Mhua protein represented by SEQ ID NO:2 is disclosed herein. The wild type MhuA gene encodes a 961 amino acid polypeptide with a predicted molecular weight of 107 KDa. The mhuA gene sequence is deposited with GenBank under accession no. AY574198.

In order to characterize MhuA as a *M. catarrhalis* protein, strain 7169, a middle-ear isolate from a child with otitis media was used to construct a MhuA deficient mutant termed 7169::mhuA which does not express the MhuA protein. 7169::mhuA was constructed using standard molecular cloning methods. Clinical isolates of *M. catarrhalis* were obtained from Mark Achtman (Max Planck Institute, Germany) or from laboratory stocks. Routine culture of *M. catarrhalis* at 35° C. in 5% $CO_2$ on brain heart infusion (BHI) or GC agar plates or at 37° C. with rotary shaking at 225 rpm in the appropriate liquid medium was performed. The mutant strain 7169::mhuA was cultured in the presence of 20 µg kanamycin per ml.

For Western blot analysis of MhuA, *M. catarrhalis* strains 7169 and 7169::mhuA were cultured in 250 ml CDM broth containing 10 µM desferal plus 5 µM Hb, 8 µM Hm, 100 µM $Fe(NO_3)_3$, or no exogenous Hb. After 16 h, cultures were harvested and outer membrane proteins (OMPs) were isolated by standard Zwittergent extraction. Proteins were analyzed by sodium dodecyl sulfate-7% polyacrylamide gel electrophoresis (SDS-7% PAGE). Western blot analyses described below with MAb 3F5 were performed using standard methods.

Figure 3B:
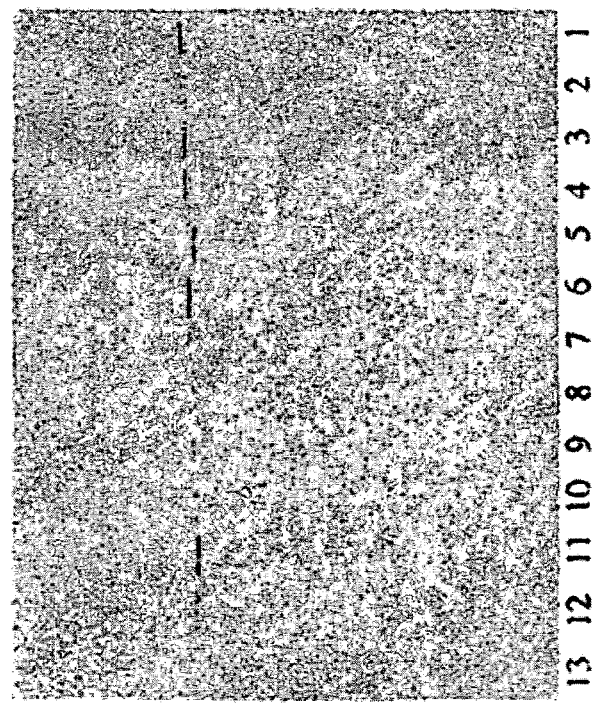
FIG. 3B is a Western blot of the gel depicted in FIG. 3A probed with a MAb specific to an external *M. catarrhalis* protein termed Mhua. The MAb with which the Western was probed is MAb 3F5-E5.
Figure 3A:
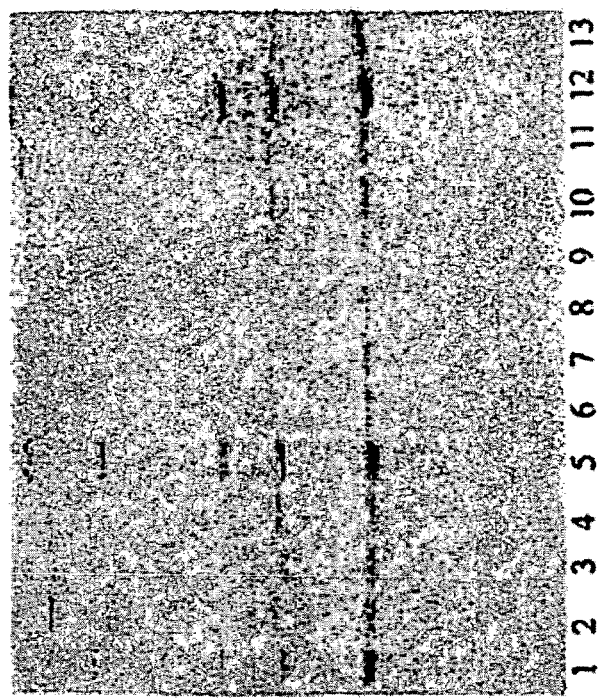
FIG. 3A is a representation of an SDS PAGE analysis of whole cell lysates from a series of *M. catarrhalis* clinical isolates from various geographical locations.

FIG. 3A is a representation of an SDS PAGE analysis of whole cell lysates from a series of *M. catarrhalis* clinical isolates from various geographical locations, while FIG. 3B is the gel from FIG. 3A probed with MAb 3F5 in a Western blot. FIGS. 3A and 3B therefore demonstrate that the 107 KDa MhuA protein is present in each *M. catarrhalis* strain tested.

Figure 4B:
FIG. 4B is a representation of a Western blot performed on the SDS PAGE gel depicted in FIG. 4A using MAb 3F5-5E5 (an IgG2a) demonstrating the loss of the 107 KDa MhuA protein band in strain 7169::mhu.
Figure 4A:
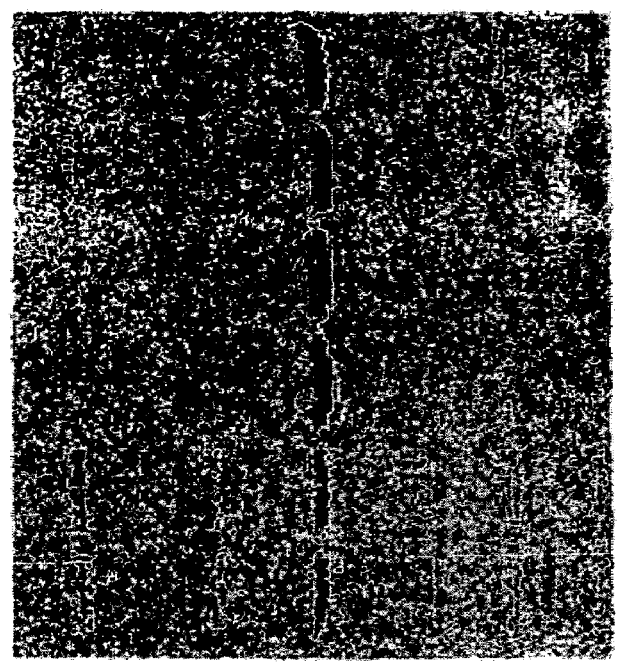
FIG. 4A is a representation of an SDS PAGE analysis of outer membrane preparations from *Moraxella catarrhalis* strains 7169 (lanes 1, 3 and 5) and 7169::mhuA (lanes 2, 4, and 6) in which the mhua gene is deleted.

In order to confirm that MhuA is an OMP, OMPs from wild-type 7169 and 7169::mhuA were prepared. Analysis of OMP profiles are depicted in the Western blot shown in FIG. 4B. FIG. 4A represents an SDS PAGE gel of proteins isolated from 7169 (lanes 1, 3 and 5) and 7169::mhuA (lanes 2, 4 and 6). FIG. 4B is a Western blot of the gel of FIG. 4A and demonstrates the loss of a 107 KDa band seen in lanes 2, 4, and 6 as expected for strain 7169::mhuA while MhuA is expressed in 7169 (FIG. 4B, lanes 1, 3, and 5).

In order to determine the level of conservation exhibited by MhuA, whole bacterial samples were prepared from a series of *M. catarrhalis* clinical isolates from various geographical locations and analyzed by Western blots probed with MAb 3F5. This data is summarized in Table 1 and demonstrates that all of the isolates express MhuA. Table 1 further demonstrates that related species of Gram-negative bacteria do not express MhuA.

In addition, many of the *M. catarrhalis* strains in Table 1 were reactive in colony lift assays, which are indicative of surface exposed epitopes. Lift assays are performed by streaking out bacteria for single colonies on a solid media, placing a sheet of nitrocellulose over the colonies, allowing the colonies to "stick" to the sheet, lifting the sheet off and analyzing the sheet as if it was a Western blot.

TABLE 1

| Strain | Reactivity to MAb 3F5 |
| --- | --- |
| *M. catarrhalis* 7169 | + |
| *M. catarrhalis* 7169::mhuA | − |
| *M. catarrhalis* isolates: | |
| CCUG 3292 (LOS serotype B) | + |
| O35E (Houston, TX, LOS serotype A) | + |
| 7544 (Ethiopia, LOS serotype A) | + |
| RS10 (LOS serotype C) | + |
| genome strain | + |
| 7477 (Japan) | + |
| 7680 (United Kingdom) | + |
| 7530 (Belgium) | + |
| 7608 (Australia) | + |
| 25240 (ATCC) | + |
| 340535 (Buffalo, NY) | + |
| CCUG 26391 (LOS serotype C) | + |
| CCUG 26404 (LOS serotype C) | + |
| *M. lacunata* | − |
| *M. bovis* | − |
| *H. ducreyi* | − |
| *H. influenzae* A2 | − |
| *N. gonorrhoeae* PID2 | − |
| *N. gonorrhoeae* F62 | − |
| *N. cinerea* | − |
| *K. pneumoniae* | − |
| *P. aeruginosa* | − |
| *P. aeruginosa* PSN | − |

Thus, the present Example demonstrates the heretofore undisclosed characterization of the MhuA gene and its expression as surface-exposed, conserved protein among *M. catarrhalis* strains that is recognized by MAb 3F5, which is capable of detecting the novel *M. catarrhalis* MhuA protein against a background of other common pathogens, some of which share a common niche and cause disease of the respiratory mucosa.

EXAMPLE 4

This Example demonstrates a MAb specific for a novel internal protein unique to *M. catarrhalis*.

Figure 5:
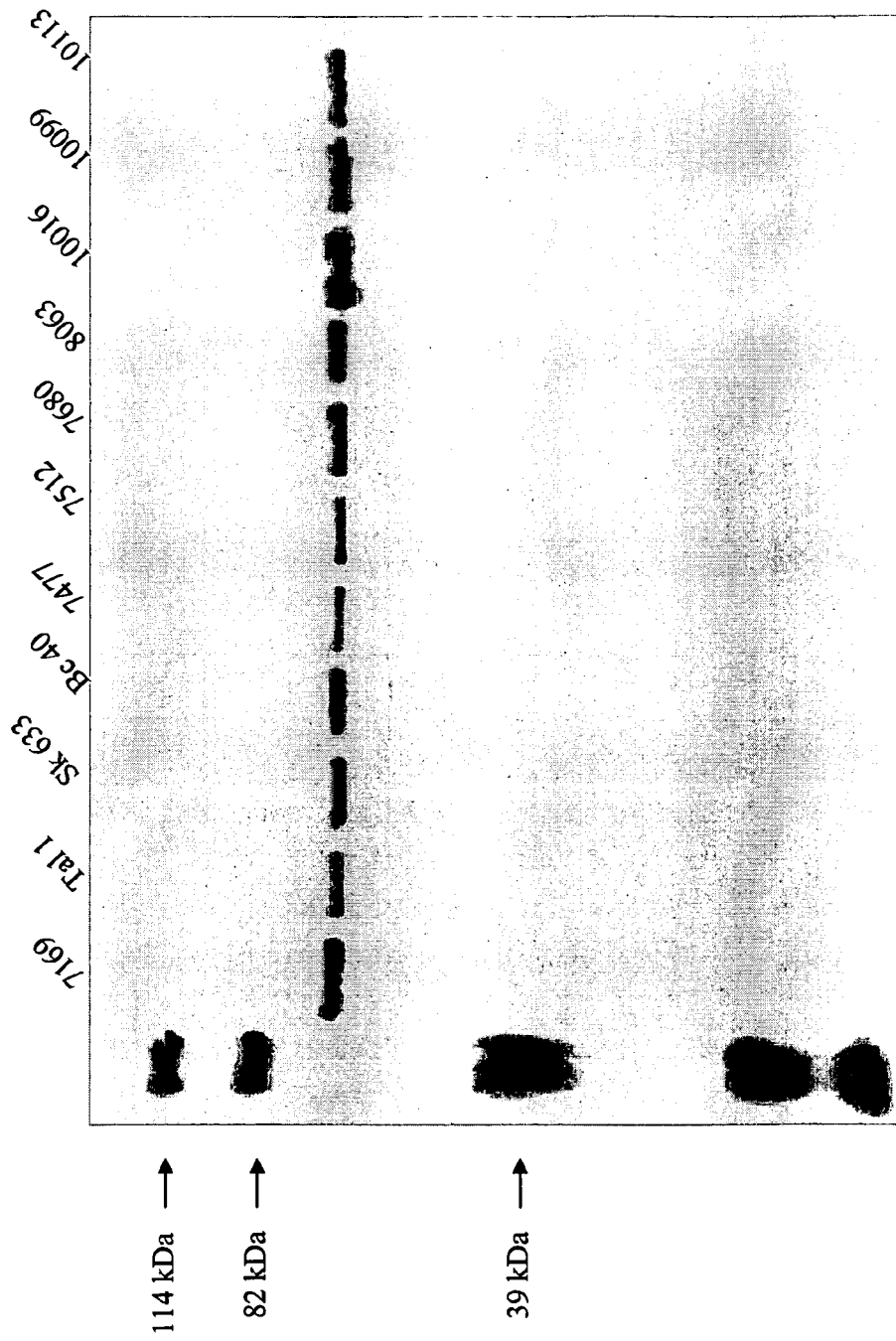
FIG. 5 is a representation of a Western blot of whole cell lysates from a series of *M. catarrhalis* clinical isolates from various geographical locations probed with a MAb specific to a *M. catarrhalis* internal protein termed Mcp67. The MAb with which the Western was probed is MAb 7C9 (an IgM). The strains shown are 7169, sk633, BC40 (Buffalo); Tall (Philadelphia); 7477 (Japan); 7512 (Belgium); 8063 (Germany); 10016 (Brazil); 10099 (Finland); 10113 (USA).

MAb 7C9 is specific for the Mcp67 internal protein of *M. catarrhalis*. MAb 7C9 was developed as described essentially as described in Example 2. As represented by the Western blot depicted in FIG. 5 and the data summarized in Table 2, the Mcp67 protein is conserved in every strain of *M. catarrhalis* tested. By using monoclonal antibody 7C9 in Western blots performed according to standard procedures, the Mcp67 protein (approximately 67 kilodaltons) has been detected in over 50 strains of *Moraxella* from around the world.

As can also be seen from Table 2, more than 25 various other gram negative strains have also been analyzed for reactivity with MAb 7C9 and all were negative. (The PCR results presented in Table 2 were generated using primers 537 (SEQ ID NO:3) and 538 (SEQ ID NO:4) as described more fully in Example 7 below).

TABLE 2

| Strain | Reactivity to Mab 7C9 | PCR Product | | |
| --- | --- | --- | --- | --- |
| *M. cat* 7169 | + | + | MEF, Child | Buffalo, NY |
| *M. cat* ATCC 25238 | | + | | |
| *M. cat* ATCC 43617 | | + | Transtracheal aspirate, Adult | |
| *M. cat* CCUG 3292 | | + | | |
| *M. cat* Rs10 | | + | | |
| *M. cat* Tal 1 | + | + | Sputum, Adult | Philadelphia, PA |
| *M. cat* BC40 | + | + | Sputum, Adult | Buffalo, NY |
| *M. cat* sk633 | + | + | Sputum, Adult | Buffalo, NY |
| *M. cat* 7431 | | + | Clinical Isolate | Columbus, OH |
| *M. cat* 7482 | | + | Clinical Isolate | Japan |
| *M. cat* 7418 | | + | Clinical Isolate | France |
| *M. cat* 7488 | | + | Clinical Isolate | Germany |
| *M. cat* 7535 | | + | Clinical Isolate | Seattle, WA |
| *M. cat* 7544 | | + | Clinical Isolate | Ethiopia |
| *M. cat* 7591 | | + | Clinical Isolate | Spain |
| *M. cat* 7966 | | + | Clinical Isolate | Australia |
| *M. cat* 10105 | | + | Clinical Isolate | Finland |
| *M. cat* 10182 | | + | Clinical Isolate | Netherlands |
| *M. cat* 7550 | | + | Clinical Isolate | Ethiopia |
| *M. cat* 8150 | | + | Clinical Isolate | Houston, TX |
| *M. cat* 7608 | | + | Clinical Isolate | Australia |
| *M. cat* 7458 | | + | Clinical Isolate | Sweden |
| *M. cat* 7587 | | + | Clinical Isolate | Spain |
| *M. cat* 7477 | + | + | Clinical Isolate | Japan |
| *M. cat* 7315 | | + | Clinical Isolate | Germany |
| *M. cat* 7574 | | + | Clinical Isolate | ChathamHospital, NC |
| *M. cat* 7512 | + | + | Clinical Isolate | Belgium |
| *M. cat* 7565 | | + | Clinical Isolate | Yugoslavia |
| *M. cat* 7480 | | + | Clinical Isolate | Japan |
| *M. cat* 7680 | + | + | Clinical Isolate | England |
| *M. cat* 7984 | | + | Clinical Isolate | Australia |
| *M. cat* 8063 | + | + | Clinical Isolate | Germany |
| *M. cat* 10016 | + | + | Clinical Isolate | Brazil |
| *M. cat* 10059 | | + | Clinical Isolate | Angola |
| *M. cat* 10099 | + | + | Clinical Isolate | Finland |
| *M. cat* 10113 | + | + | Clinical Isolate | USA |
| *M. cat* 10188 | | + | Clinical Isolate | Netherlands |
| *M. cat* 10218 | | + | Clinical Isolate | Africa |
| *M. cat* pw640 | + | | Sputum, Adult | England |
| *M. cat* Af218 | + | | Sputum, Adult | England |
| *M. cat* M10 | + | | Sputum, Adult | Houston, TX |
| *M. cat* O35E | + | | MEF, child | Houson, TX |

Additional tests have confirmed that c protein is not present on the surface of the bacteria and the protein has no significant homology with any other protein in the current data base. Further, as can be seen from Table 3, MAb 7C9 does not react to any other bacterial strains tested.

TABLE 3

| Bacterial Strain | Reactivity to Mab 7C9 | PCR Product |
| --- | --- | --- |
| *H. influenzae* 1479 | − | − |
| Non-typeable *H. influenzae* 2019 | − | − |
| Non-typeable *H. influenzae* 3198 | − | − |
| *H. ducreyi* R3 | − | − |
| *H. ducreyi* CIP 542 | − | − |
| *H. ducreyi* HP35000 | − | − |
| Psn | − | − |
| Psc | − | − |
| *N. gonorrhoeae* F62 | − | − |
| *N. gonorrhoeae* PID2 | − | − |
| *N. gonorrhoeae* FA19 | − | − |
| *M. bovis* | − | − |

TABLE 3-continued

| Bacterial Strain | Reactivity to Mab 7C9 | PCR Product |
|---|---|---|
| M. nonliquifaciens | − | − |
| M. lacunata | − | − |
| M. osloensis | − | − |
| M. caviae | − | − |
| P. aeruginosa | − | − |
| N. cinerea | − | − |
| K. pneumoniae | − | − |
| E. aerogenes | − | − |
| N. gonorrhoeae 1 | − | − |
| N. gonorrhoeae 2 | − | − |
| N. gonorrhoeae 3 | − | − |
| N. gonorrhoeae 4 | − | − |
| N. gonorrhoeae 5 | − | − |
| N. gonorrhoeae 6 | − | − |
| N. gonorrhoeae 7 | − | − |
| N. gonorrhoeae 8 | − | − |
| N. gonorrhoeae 9 | − | − |
| N. gonorrhoeae 10 | − | − |
| H. parainfluenzae 7P10 | − | − |
| H. parainfluenzae 9P20 | − | − |
| H. parainfluenzae 6P30 | − | − |
| H. parainfluenzae 15P0 | − | − |
| H. influenzae 7502 | − | − |
| H. influenzae 4971 | − | − |
| K. oxytoca | − | − |
| P. mirabilis | − | − |
| E. coli | − | − |
| M. cuniculi | − | − |

Thus, this Example demonstrates a MAb that can detect a novel protein unique to *M. catarrhalis*. That nucleotide sequence represented by SEQ ID NO:5 encodes the Mcp67 protein represented by SEQ ID NO:6 is disclosed herein.

EXAMPLE 5

This Example demonstrates DNA sequences that are unique to *M. catarrhalis*.

The Example further describes a method for using PCR analysis of the DNA sequences to distinguish *M. catarrhalis* from other organisms and to distinguish between the three *M. catarrhalis* LOS serotypes.

*M. catarrhalis* chromosomal DNA was prepared using standard methods. All standard molecular biology reagents, including T4 ligase and restriction endonucleases, were purchased from either Promega (Madison, Wis.) or New England Biolabs, Inc. (Beverly, Mass.) and were utilized according to standard protocols. PCR amplification analyses were performed using genomic *M. catarrhalis* 7169 DNA with Platinum Taq High Fidelity Polymerase (Invitrogen Life Technologies Corp., Carlsbad, Calif.). All PCR products and plasmid constructs were purified using the MinElute kit and the QIAprep spin kit, respectively (Qiagen). DNA sequencing was performed (RPCI Biopolymer Facility, Roswell Park Cancer Institute, Buffalo, N.Y.) and analyzed with MacVector software (version 7.2; Genetics Computer Group, Madison, Wis.).

Novel PCR primers were designed to amplify previously undisclosed differences in putative glycosyltransferase (pgt) genes unique to *M. catarrhalis* strains. Accordingly, using standard PCR protocols, combinations of the primers disclosed herein can be used to amplify regions of clustered genes from *M. catarrhalis* in a manner such that all three serotypes A, B and C can be distinguished from one another, and *M. catarrhalis* can be distinguished from other organisms.

Figure 7:
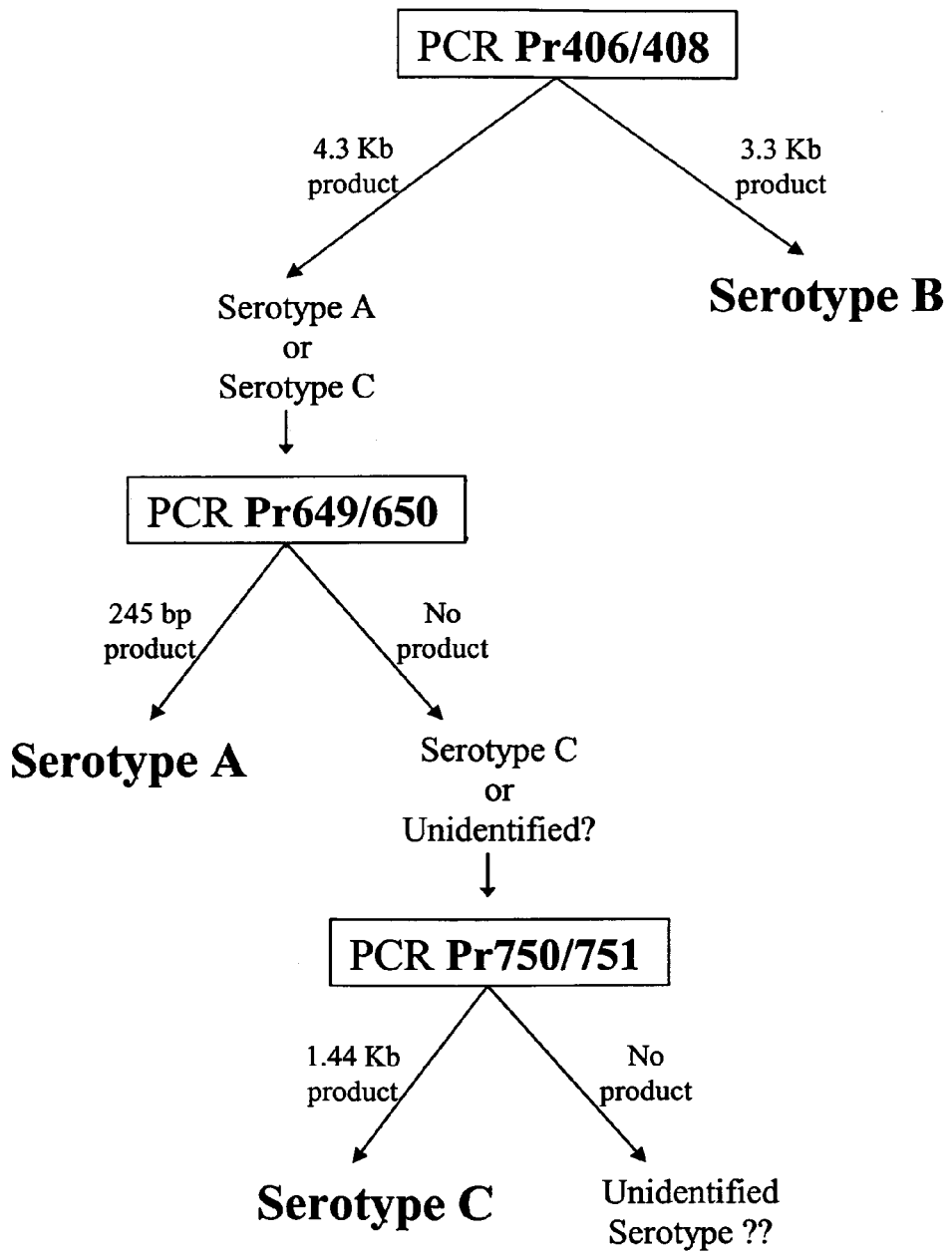
FIG. 7 is a graphical representation of a PCR based scheme by which all three serotypes of *M. catarrhalis* can be distinguished from each other.

The PCR primers used in this Example are summarized in Table 4. A flow chart for performing the steps of this identification strategy is presented in FIG. 7. Further, the genomic organization of the *Moraxella catarrhalis* LOS serotype defining pgt genes is depicted in FIG. 8.

Figure 8:
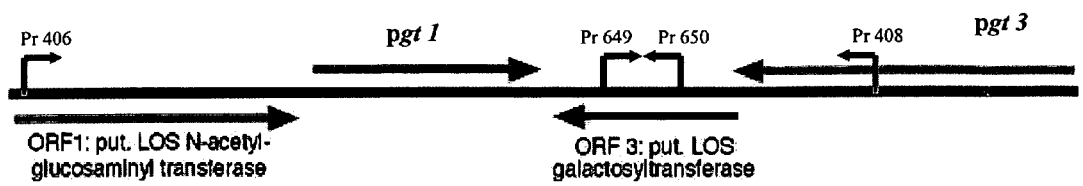
FIG. 8 is a graphical representation of PCR primers and targets within the *M. catarrhalis* putative glycosyltransferase (pgt) gene cluster.
Figure 8:
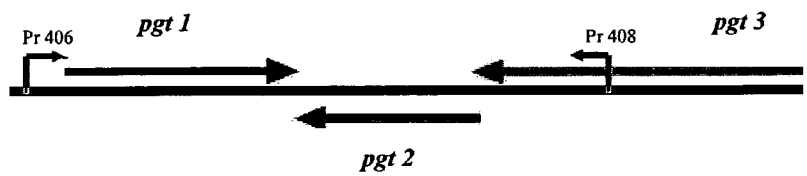
Figure 8:
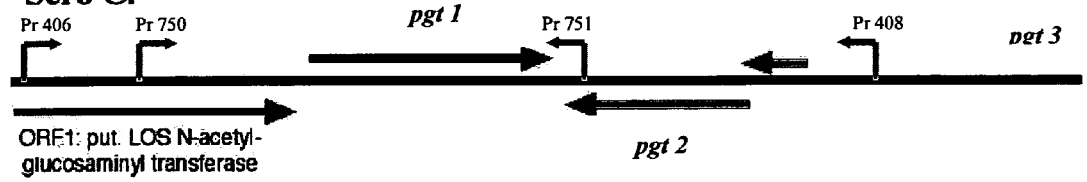

The LOS gene cluster from 25238 (type A) as shown in FIG. 8 is represented by SEQ ID NO:15. With respect to SEQ ID NO:15, primer 406 binds from position 1-22, primer 408 binds from position 4292-4310, primer 649 binds from position 2379-2399 and primer 650 binds from position 2605-2624. Primers 750/751 do not bind to SEQ ID NO:15.

The LOS gene cluster from strain 7169 (type B) as shown in FIG. 8 is represented by SEQ ID NO:16. With respect to SEQ ID NO:16, primer 406 binds from position 1-22, primer 408 binds from position 3295-3313. Primers 649/650 and 750/751 do not bind to SEQ ID NO:16.

The LOS gene cluster from RS-10 (type C) as shown in FIG. 8 is represented by SEQ ID NO:17. With respect to SEQ ID NO:17, primer 406 binds from position 1-22, primer 408 binds from position 4306-4324, primer 750 binds from position 822-840, and primer 751 binds from position 2239-2258. Primers 649/650 do not bind to SEQ ID NO:17.

TABLE 4

| | | |
|---|---|---|
| Pr 406 (SEQ ID NO:7) | | CAAAAGAAGACAAACAAGCAGC |
| Pr 408 (SEQ ID NO:8) | | CCCATTTAGTATCAGAAGATGACAC |
| Pr 649 (SEQ ID NO:9) | | ATCCTGCTCCAACTGACTTTC |
| Pr 650 (SEQ ID NO:10) | | GGTAACAGAACGCTCAACCC |
| Pr 750 (SEQ ID NO:11) | | CCAAGGGGCTGATTTGACA |
| Pr 751 (SEQ ID NO:12) | | ACTATCAGTAACCAGGTTTT |

Figure 6:
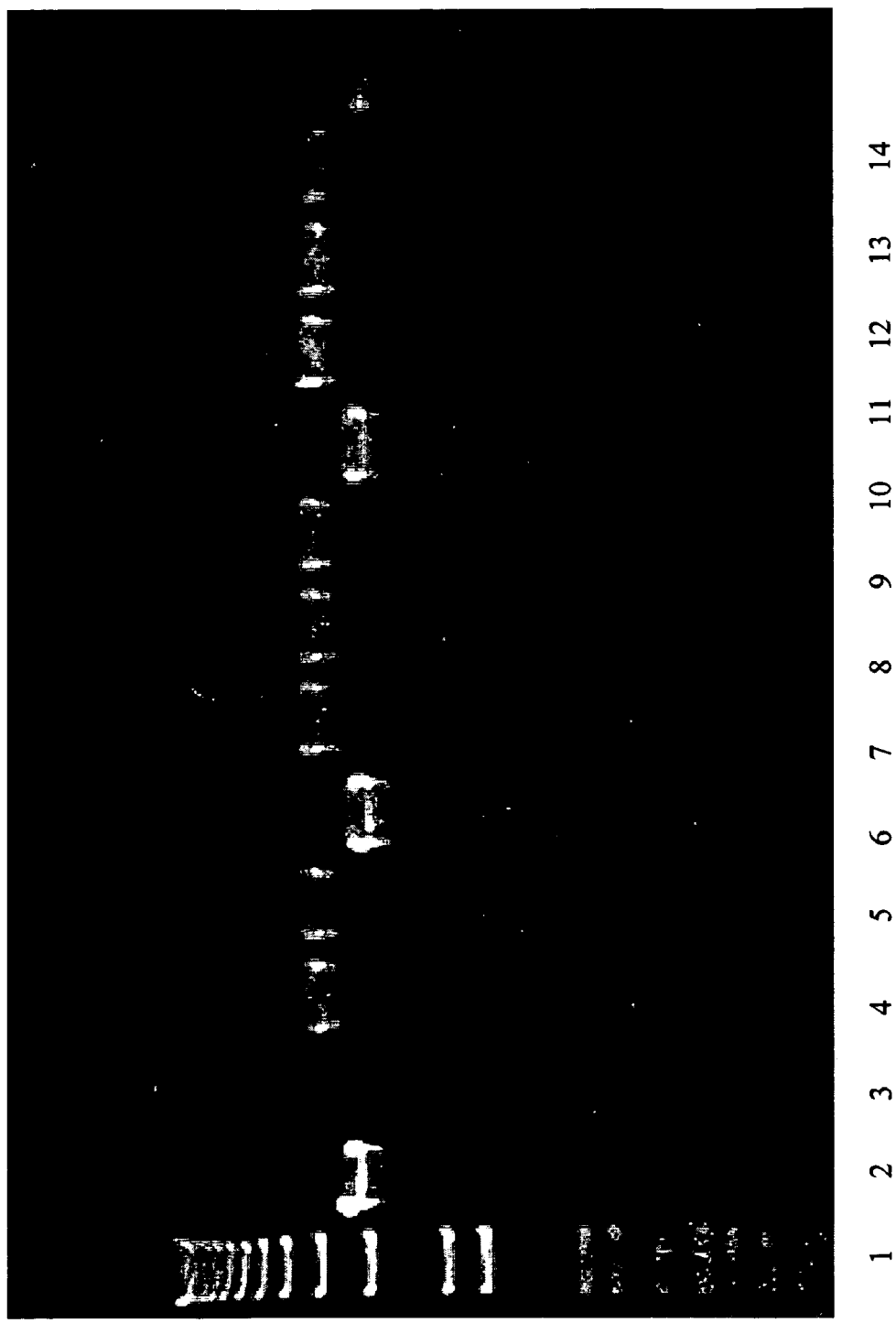
FIG. 6 is a representation of an agarose gel showing PCR products amplified from chromosomal DNA isolated from *M. catarrhalis* strains. The PCR products in each lane were amplified using the primers 406/408. Lane 1 is a size ladder. Lane 2 is amplification of genomic DNA from strain 7169 and the resulting product is 3.3 Kb. Lane 3 is the negative control (no DNA in PCR reaction). Lanes 4, 5, 7, 8, 9, 11, 12 and 13 contain an approximate 4.3 Kb are each serotype A or C. A 3.3 Kb band in lane 6 size was obtained by analyzing the only previously reported LOS serotype B strain, *M. catarrhalis* CCUG 3292, demonstrating strain 7169 as shown in Lane 2 is also serotype B. Lanes 6, 10 and 14 are other *Moraxella* isolates that were determined to be serotype B.

In LOS serotypes A and C primers 406 and 408 amplify an approximately 4.3 kB product, while in serotype B primers 406 and 408 amplify an approximately 3.3 kB product. This is demonstrated in FIG. 6 which is a representation of an agarose gel showing PCR products amplified from chromosomal DNA isolated from *M. catarrhalis* strains. The PCR products in each lane were amplified using the primers 406/408. Lane 1 is a size ladder. Lane 2 is amplification of genomic DNA from strain 7169 and the resulting product is 3.3 Kb. Lane 3 is the negative control (no DNA in PCR reaction). A 3.3 Kb band in lane 6 size was obtained by analyzing the only previously reported LOS serotype B strain, *M. catarrhalis* CCUG 3292, demonstrating strain 7169 is also serotype B. Lanes 4, 5, 7, 8, 9, 11, 12 and 13 contain an approximate 4.3 Kb are each serotype A or C. Lanes 6, 10 and 14 are other *Moraxella* isolates that were determined to be serotype B.

Using primers 649 and 650 results in amplification of a 246 bp fragment from LOS serotype A and no amplification in serotypes B and C. Further, using primers 750 and 751 results in amplification of a 1.44 kB product in serotype C, but no amplification in serotypes A and B. These results are summarized in Table 5.

TABLE 5

| | Pr 406/408 | Pr 649/650 | Pr 750/751 |
|---|---|---|---|
| Serotype A | 4.3 kb | 245 bp | N/A |
| Serotype B | 3.3 kb | N/A* | N/A |
| Serotype C | 4.3 kb | N/A | 1.44 kb |

Thus, by performing PCR reactions using combinations of the primers disclosed herein, one can distinguish all three serotypes A, B and C from one another.

Primers 406 and 408 were tested on genomic DNA isolated from *Neisseria meningitidis* 121, *Neisseria gonorrhoeae, Haemophilus influenzae* (7 strains), *Haemophilus ducreyi* CIP542, *Haemophilus ducreyi* 35000, *Haemophilus parainfluenzae, Klebsiella pneumoniae, Enterobacter aerogenes, Escherichia coli* CP9, *Psuedomonas aeruginosa*, and *Proteus mirabilis*.

Thus, this Example demonstrates the identification of novel DNA sequences that can be used to detect *M. catarrhalis* in a biological sample and to discriminate between *M. catarrhalis* LOS serotypes. Further, the present examples illustrates primers and a PCR scheme for definitive identification of each *M. catarrhalis* LOS serotype.

EXAMPLE 6

This Example demonstrates DNA sequences encoding a novel surface protein unique to *M. catarrhalis* and methods for the identification of the DNA sequences.

*M. catarrhalis* chromosomal DNA was prepared and PCR reactions carried out essentially as described in Example 5 and the MhuA surface protein of *M. catarrhalis* was identified through BLAST searches based on homology to other TonB-dependent proteins in the National Center for Biotechnology Information (NCBI) data bank. PCR primers were designed for cloning mhuA based on its nucleotide sequence, accession number AX067431. PCR amplification of 75 bp upstream of the predicted 5' transcription start site and 197 bp upstream of the 3' predicted stop site was performed using primers 605 and 606 as depicted in Table 6.

TABLE 6

| Pr 605 (SEQ ID NO:13) | TGATTGGTGATAAAAGTAGG |
|---|---|
| Pr 606 (SEQ ID NO:14) | TGTTGGCATCTAAGGGGTC |

PCR analysis of primers 605 and 606 resulted in a 2782 bp product that was ligated into pGEM-T Easy (Promega), resulting in pTB6-AH. *E. Coli* XL1-Blue were transformed with pTB6-AH using electroporation. PCR analysis, restriction digestion, and sequence analysis were performed using this plasmid to confirm the nucleotide organization of the 7169 mhuA as shown in SED ID NO:1.

As indicated in Table 7, PCR reactions performed on genomic DNA of various organisms using primers 605 and 606 results in amplification of genomic DNA in all *M. catarrhalis* strains tested and in no amplification in non-*M. catarrhalis* strains.

TABLE 7

| Strain | PCR result (primers 605 and 606) |
|---|---|
| *M. catarrhalis* strains: | |
| 7169 | + |
| 7169::mhuA | − |
| 43617 (genome strain) | + |
| RS10 | + |
| 7680 (Mark Achtman) | + |
| 7608 (MA) | + |
| 7477 (MA) | + |
| 7544 (MA) | + |

TABLE 7-continued

| Strain | PCR result (primers 605 and 606) |
|---|---|
| Non-*M. catarrhalis* strains: | |
| *M. bovis* | − |
| *Haemophilus influenzae* 5657 | − |
| *Neisseria cinerea* 658 | − |
| *N. gonorrhoeae* 3 | − |
| *Pseudomonas aeruginosa* PSN | − |
| *H. influenzae* 2019 | − |
| *N. gonorrhoeae* 4 | − |
| *Klebsiella pneumoniae* | − |

Further and as will be apparent to those skilled in the art, because the DNA sequence encoding MhuA has been shown to be unique to *M. catarrhalis*, amplification of any part of the sequence will specifically detect *M. catarrhalis* in a biological sample.

EXAMPLE 7

This Example demonstrates the detection of nucleic acid sequence encoding a novel internal protein unique to *M. catarrhalis*.

As demonstrated in Example 4 above using MAb 7C9, the Mcp67 protein is expressed in every strain of *Moraxella* tested to date. This Example provides a method for identifying the DNA sequences of the gene encoding the Mcp67 protein.

Using PCR analysis with the primers depicted in Table 8, over 50 strains of *M. catarrhalis* were tested and were positive for the Mcp67 gene DNA. The gene encoding the Mcp67 protein is represented by SEQ ID NO:5 and the Mcp67 amino acid sequence is represented by SEQ ID NO:6. These results are presented in Table 3 and are further demonstrated in FIGS. 9A and 9B.

TABLE 8

| Pr 537 (SEQ ID NO:3) | GCCAATGCTTTGCCTGATAATGAG |
|---|---|
| Pr 538 (SEQ ID NO:4) | TGGTGTTTTGACTGGGGTGGTAG |

These primers are designed to the N-terminal internal portion of the gene that codes for the Mcp67 protein and amplify a product from nucleotide 566 to 994 of SEQ ID NO:5.

Figure 9A:
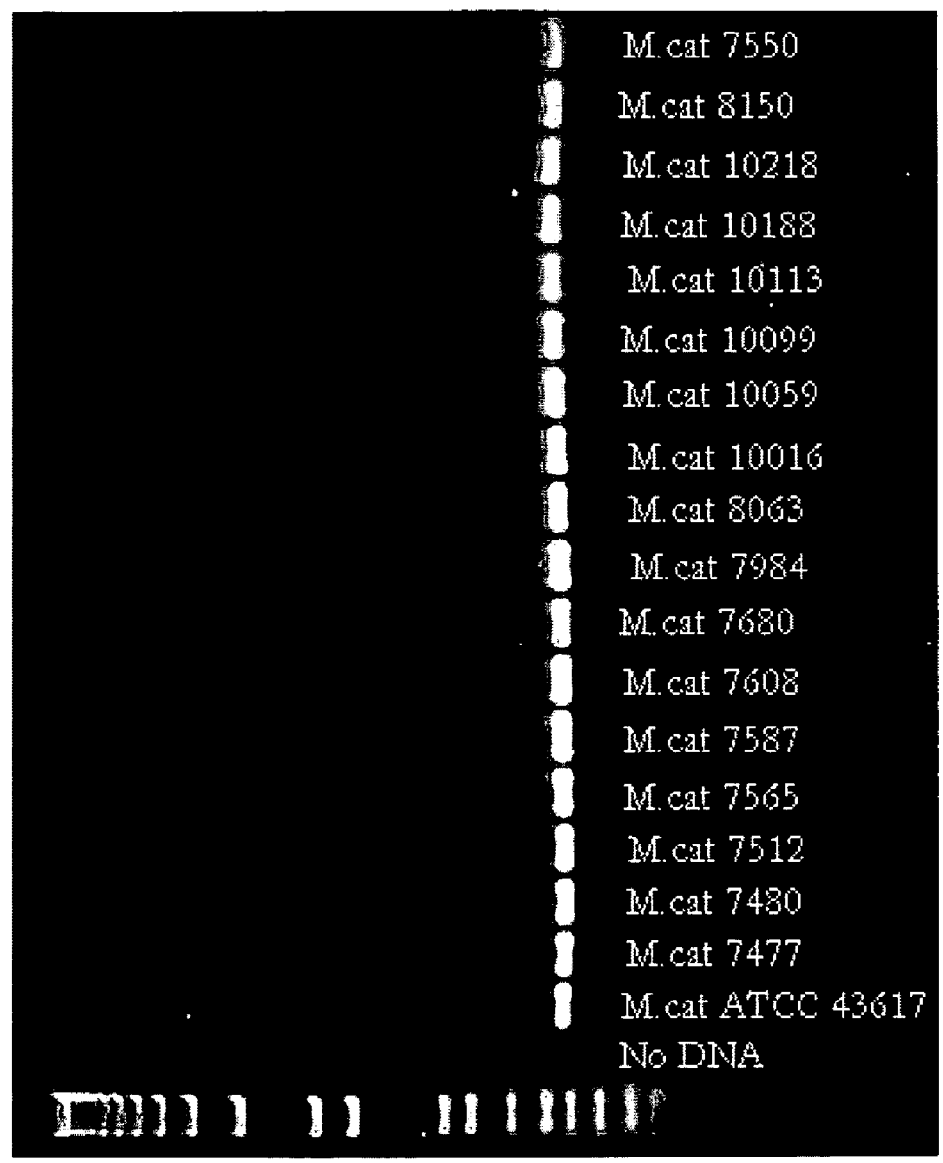
FIG. 9A is a graphical depiction of PCR amplifications of genomic DNA from various *M. catarrhalis* strains. The PCR amplifications in FIGS. 9A and 9B were carried out with primers SEQ ID NO:3 and SEQ ID NO:4.
Figure 9B:
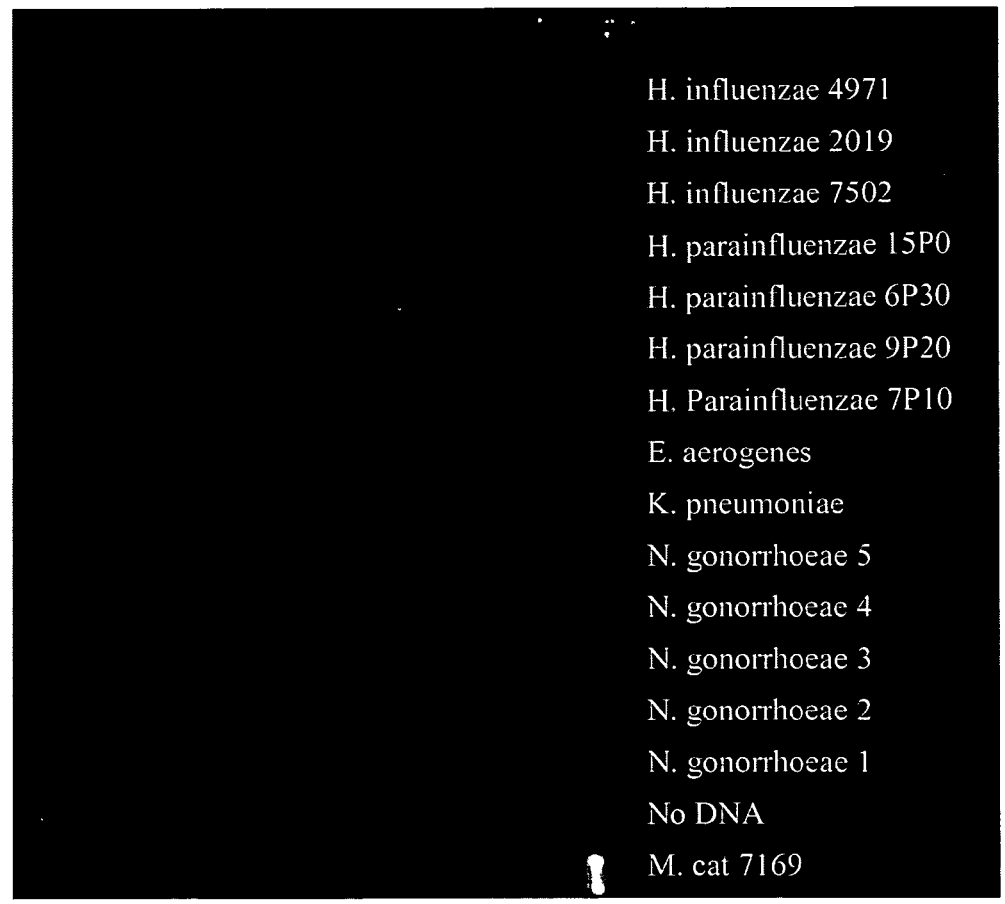
FIG. 9B is a graphical depiction of PCR amplifications of genomic DNA from *M. catarrhalis* in lane 1 and various other non *M. catarrhalis* organisms in the remaining lanes as indicated.

FIGS. 9A and 9B depict PCR analysis using primers 537 and 538 demonstrating the presence of the Mcp67 gene in *M. catarrhalis* and the lack of amplification products in PCR analysis performed on a variety of other infectious bacterial species.

Further, Table 9 demonstrates results for both PCR analysis of the Mcp67 gene from clinical isolates from around the world in conjunction with antibody based detection of the Mcp67 protein using MAb 7C9.

TABLE 9

| Strain | Reactivity to Mab 7C9 | PCR Product | | |
|---|---|---|---|---|
| *M. cat* 7169 | + | + | MEF, Child | Buffalo, NY |
| *M. cat* ATCC 25238 | + | + | | |
| *M. cat* ATCC | + | + | Transtracheal | |

TABLE 9-continued

| Strain | Reactivity to Mab 7C9 | PCR Product | | |
|---|---|---|---|---|
| 43617 | | | aspirate, Adult | |
| M. cat CCUG 3292 | + | + | | |
| M. cat Rs10 | | + | | |
| M. cat Tal 1 | + | + | Sputum, Adult | Philadelphia, PA |
| M. cat BC40 | + | + | Sputum, Adult | Buffalo, NY |
| M. cat sk633 | + | + | Sputum, Adult | Buffalo, NY |
| M. cat 7431 | + | + | Clinical Isolate | Columbus, OH |
| M. cat 7482 | + | + | Clinical Isolate | Japan |
| M. cat 7418 | + | + | Clinical Isolate | France |
| M. cat 7488 | + | + | Clinical Isolate | Germany |
| M. cat 7535 | + | + | Clinical Isolate | Seattle, WA |
| M. cat 7544 | + | + | Clinical Isolate | Ethiopia |
| M. cat 7591 | + | + | Clinical Isolate | Spain |
| M. cat 7966 | + | + | Clinical Isolate | Australia |
| M. cat 10105 | + | + | Clinical Isolate | Finland |
| M. cat 10182 | + | + | Clinical Isolate | Netherlands |
| M. cat 7550 | + | + | Clinical Isolate | Ethiopia |
| M. cat 8150 | + | + | Clinical Isolate | Houston, TX |
| M. cat 7608 | + | + | Clinical Isolate | Australia |
| M. cat 7458 | + | + | Clinical Isolate | Sweden |
| M. cat 7587 | + | + | Clinical Isolate | Spain |
| M. cat 7477 | + | + | Clinical Isolate | Japan |
| M. cat 7315 | + | + | Clinical Isolate | Germany |
| M. cat 7574 | + | + | Clinical Isolate | ChathamHospital, NC |
| M. cat 7512 | + | + | Clinical Isolate | Belgium |
| M. cat 7565 | + | + | Clinical Isolate | Yugoslavia |
| M. cat 7480 | + | + | Clinical Isolate | Japan |
| M. cat 7680 | + | + | Clinical Isolate | England |
| M. cat 7984 | + | + | Clinical Isolate | Australia |
| M. cat 8063 | + | + | Clinical Isolate | Germany |
| M. cat 10016 | + | + | Clinical Isolate | Brazil |
| M. cat 10059 | + | + | Clinical Isolate | Angola |
| M. cat 10099 | + | + | Clinical Isolate | Finland |
| M. cat 10113 | + | + | Clinical Isolate | USA |
| M. cat 10188 | + | + | Clinical Isolate | Netherlands |
| M. cat 10218 | + | + | Clinical Isolate | Africa |
| M. cat pw640 | + | + | Sputum, Adult | England |
| M. cat Af218 | + | + | Sputum, Adult | England |
| M. cat M10 | + | + | Sputum, Adult | Houston, TX |
| M. cat O35E | + | + | MEF, child | Houson, TX |

Moreover, Table 10 demonstrates that a wide variety of organisms other M. catarrhalis are not detected by MAb 7C9 or PCR amplification.

TABLE 10

| Bacterial Strain | Reactivity to Mab 7C9 | PCR Product |
|---|---|---|
| H. influenzae 1479 | − | − |
| Non-typeable H. influenzae 2019 | − | − |
| Non-typeable H. influenzae 3198 | − | − |
| H. ducreyi R3 | − | − |
| H. ducreyi CIP 542 | − | − |
| H. ducreyi HP35000 | − | − |
| Psn | − | − |
| Psc | − | − |
| N. gonorrhoeae F62 | − | − |
| N. gonorrhoeae PID2 | − | − |
| N. gonorrhoeae FA19 | − | − |
| M. bovis | − | − |
| M. nonliquifaciens | − | − |
| M. lacunata | − | − |
| M. osloensis | − | − |
| M. caviae | − | − |
| P. aeruginosa | − | − |
| N. cinerea | − | − |
| K. pneumoniae | − | − |
| E. aerogenes | − | − |
| N. gonorrhoeae 1 | − | − |

TABLE 10-continued

| Bacterial Strain | Reactivity to Mab 7C9 | PCR Product |
|---|---|---|
| N. gonorrhoeae 2 | − | − |
| N. gonorrhoeae 3 | − | − |
| N. gonorrhoeae 4 | − | − |
| N. gonorrhoeae 5 | − | − |
| N. gonorrhoeae 6 | − | − |
| N. gonorrhoeae 7 | − | − |
| N. gonorrhoeae 8 | − | − |
| N. gonorrhoeae 9 | − | − |
| N. gonorrhoeae 10 | − | − |
| H. parainfluenzae 7P10 | − | − |
| H. parainfluenzae 9P20 | − | − |
| H. parainfluenzae 6P30 | − | − |
| H. parainfluenzae 15P0 | − | − |
| H. influenzae 7502 | − | − |
| H. influenzae 4971 | − | − |
| K. oxytoca | − | − |
| P. mirabilis | − | − |
| E. coli | − | − |
| M. cuniculi | − | − |

Thus, this Example demonstrates the detection of nucleic acid sequences encoding a novel internal protein unique to M. catarrhalis. Further and as will be apparent to those skilled in the art, because the DNA sequence encoding Mcp67 has been shown to be unique to M. catarrhalis, amplification of any part of the sequence will specifically detect M. catarrhalis in a biological sample.

EXAMPLE 8

This Example demonstrates that using combinations of the antibodies of the present invention results in increased detection of M. catarrhalis proteins.

Table 11 summarizes data from a variety of ELISA assays using the MAbs indicated in the top row. The assays were performed as follows:

Approximately $10^6$-$10^7$ M. catarrhalis 7169 whole bacteria were added to each well of a 96 well ELISA plate. The bacteria were allowed to coat the wells for 24 hours at 40 C and the wells were washed and blocked for 1 hour with 2% milk in PBS. The wells were washed and 100 microliters of each antibody was added and than removed after 1 hour.

The data summarized in Table 11 demonstrates increased detection of M. catarrhalis by using combinations of the MAbs of the present invention. The positive control was mouse sera from animals injected with M, catarrhalis strain 7169 and the negative control was normal mouse sera. Further, the data in the bottom row of Table 8 was obtained after adding a mild detergent to the bacteria in the wells and demonstrates enhanced detection, particularly when an antibody to the internal Mcp67 protein (i.e., MAb 7C9) is used.

TABLE 11

| Mab 4G5 | +Mab 3F7 | +Mab 3F5 | +Mab 7C9 | Positive | Negative |
|---|---|---|---|---|---|
| 0.422 | 0.605 | 0.987 | 1.020 | 0.320 | 0.075 |
| 0.553 | 0.721 | 1.230 | 1.423 | 0.356 | 0.068 |

What is claimed is:

1. A method of identifying *Moraxella catarrhalis* lipooligosaccharide (LOS) serotypes in a biological sample comprising the step of:

contacting a first aliquot from the sample with monoclonal antibody 4G5 which recognizes *Moraxella catarrhalis* serotypes A, B and C, wherein the 4G5 monoclonal antibody is produced by a cell culture having deposit designation PTA-8544, and contacting at least a second aliquot of the sample with a monoclonal antibody that is specific for the B serotype, wherein detecting binding of the 4G5 monoclonal antibody and the monoclonal antibody that is specific for the B serotype is indicative of the *Moraxella catarrhalis* LOS serotype in the sample as B serotype, and wherein detecting binding of the 4G5 monoclonal antibody but not detecting binding of the monoclonal antibody that is specific for B serotype is indicative of the *Moraxella catarrhalis* LOS serotype in the sample as A or C serotype.

2. The method of claim 1, wherein the binding of the monoclonal antibody which recognizes *Moraxella catarrhalis* serotypes A, B and C and the binding of a monoclonal antibody that is specific for the B serotype is by measured by a method selected from the group of Western blotting, enzyme-linked immunosorbent assay, radioimmunoassays, and immunochromatographic strip assay.

3. The method of claim 2, wherein the binding of the monoclonal antibody which recognizes *Moraxella catarrhalis* serotypes A, B and C and the binding of a monoclonal antibody that is specific for the B serotype is by measured by immunochromatographic strip assay.

* * * * *